United States Patent
Scheller et al.

(10) Patent No.: US 10,070,923 B2
(45) Date of Patent: *Sep. 11, 2018

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,927

(22) Filed: Aug. 23, 2017

(65) Prior Publication Data
US 2017/0367763 A1    Dec. 28, 2017

Related U.S. Application Data

(63) Continuation of application No. 13/938,635, filed on Jul. 10, 2013, now Pat. No. 9,770,296.

(51) Int. Cl.
*A61B 18/18*    (2006.01)
*A61B 18/22*    (2006.01)
(Continued)

(52) U.S. Cl.
CPC .......... *A61B 18/22* (2013.01); *A61F 9/00821* (2013.01); *A61B 18/20* (2013.01);
(Continued)

(58) Field of Classification Search
CPC .............................. A61B 18/22; A61F 9/00821
See application file for complete search history.

(56) References Cited

U.S. PATENT DOCUMENTS 3,174,851 A    3/1965    Buehler et al.
4,122,853 A    10/1978    Smith
(Continued)

FOREIGN PATENT DOCUMENTS

EP    EP 0900547 B1    3/1999
GB    2208805 A    4/1989
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — William Thomson
*Assistant Examiner* — Sebastian X Lukjan

(57) ABSTRACT

A steerable laser probe may include a handle having a handle distal end and a handle proximal end, a plurality of actuation controls of the handle, a flexible housing tube having a flexible housing tube distal end and a flexible housing tube proximal end, and an optic fiber disposed within an inner bore of the handle and the flexible housing tube. An actuation of an actuation control of the plurality of actuation controls may gradually curve the flexible housing tube. A gradual curving of the flexible housing tube may gradually curve the optic fiber. An actuation of an actuation control of the plurality of actuation controls may gradually straighten the flexible housing tube. A gradual straightening of the flexible housing tube may gradually straighten the optic fiber.

20 Claims, 28 Drawing Sheets

(51) Int. Cl.
    *A61B 18/20*     (2006.01)
    *A61F 9/008*     (2006.01)

(52) U.S. Cl.
    CPC ............... *A61B 2018/2238* (2013.01); *A61F 2009/00863* (2013.01)

(56) References Cited

U.S. PATENT DOCUMENTS

| | | |
|---|---|---|
| 4,147,443 A | 4/1979 | Skobel |
| 4,687,293 A | 8/1987 | Randazzo |
| 4,744,360 A | 5/1988 | Bath |
| 4,870,952 A | 10/1989 | Martinez |
| 5,190,050 A | 3/1993 | Nitzsche |
| 5,228,852 A | 7/1993 | Goldsmith et al. |
| 5,257,988 A | 11/1993 | L'Esperance, Jr. |
| 5,322,055 A | 6/1994 | Davison et al. |
| 5,322,064 A | 6/1994 | Lundquist |
| 5,346,504 A | 9/1994 | Ortiz et al. |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,735,842 A | 4/1998 | Kruege et al. |
| 5,855,577 A | 1/1999 | Murphy-Chutorian et al. |
| 5,873,865 A | 2/1999 | Horzewski et al. |
| 5,951,544 A | 9/1999 | Konwitz |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,330,837 B1 | 12/2001 | Charles et al. |
| 6,352,531 B1 | 3/2002 | O'Connor et al. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,554,794 B1 | 4/2003 | Mueller et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 | 3/2005 | Sonnenschein et al. |
| 6,984,230 B2 | 1/2006 | Scheller et al. |
| 7,004,957 B1 | 2/2006 | Dampney et al. |
| 7,090,411 B2 * | 8/2006 | Brown ................. G02B 6/4296 385/78 |
| 7,226,444 B1 | 6/2007 | Ellman et al. |
| 7,303,533 B2 | 12/2007 | Johansen et al. |
| 7,402,158 B2 | 7/2008 | Scheller et al. |
| 7,555,327 B2 | 6/2009 | Matlock |
| 7,632,242 B2 | 12/2009 | Griffin et al. |
| 7,766,904 B2 | 10/2010 | McGowan, Sr. et al. |
| 7,935,108 B2 | 5/2011 | Baxter et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,968,277 B2 | 1/2015 | Scheller et al. |
| 8,951,245 B2 | 2/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0131399 A1 | 6/2005 | Loeb et al. |
| 2005/0131400 A1 * | 6/2005 | Hennings ............... A61B 18/24 606/15 |
| 2005/0154379 A1 | 7/2005 | McGowan et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeny et al. |
| 2005/0277874 A1 | 12/2005 | Selkee |
| 2006/0129175 A1 | 6/2006 | Griffen et al. |
| 2006/0178674 A1 | 8/2006 | McIntyre |
| 2006/0293270 A1 | 12/2006 | Adamis et al. |
| 2007/0179475 A1 | 8/2007 | Scheller |
| 2007/0185514 A1 | 8/2007 | Kirchhevel |
| 2007/0260231 A1 | 11/2007 | Rose et al. |
| 2008/0132761 A1 | 6/2008 | Sonnenschein et al. |
| 2008/0208105 A1 | 8/2008 | Zelickson et al. |
| 2008/0287938 A1 | 11/2008 | Scheller et al. |
| 2009/0018993 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 * | 1/2010 | Lumpkin ................. A61B 18/22 606/4 |
| 2010/0191224 A1 | 7/2010 | Butcher |
| 2010/0268234 A1 | 10/2010 | Aho et al. |
| 2010/0331883 A1 | 12/2010 | Schmitz et al. |
| 2011/0028947 A1 | 2/2011 | Scheller et al. |
| 2011/0144627 A1 | 6/2011 | Smith |
| 2011/0144630 A1 | 6/2011 | Loeb |
| 2011/0190749 A1 | 8/2011 | McMillian et al. |
| 2011/0280653 A1 | 11/2011 | Sjostedt et al. |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 * | 4/2013 | Mansour ............. A61F 9/00821 606/4 |
| 2013/0096541 A1 | 4/2013 | Scheller et al. |
| 2013/0116671 A1 | 5/2013 | Scheller et al. |
| 2013/0144278 A1 | 6/2013 | Papac et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |
| 2017/0135859 A1 | 5/2017 | Scheller et al. |

FOREIGN PATENT DOCUMENTS

| | | |
|---|---|---|
| WO | WO 2011/019581 A1 | 2/2001 |
| WO | WO 2006/091597 A1 | 8/2006 |
| WO | WO 2007/038433 A2 | 4/2007 |
| WO | WO 2013/133717 | 9/2013 |

OTHER PUBLICATIONS

Terry P.W. Melchels, Jan Feijen, Dirk W. Grijpma, A review on stereolithography and its applications in biomedical engineering, Biomaterials 31 (2010) 6121-6130.

* cited by examiner

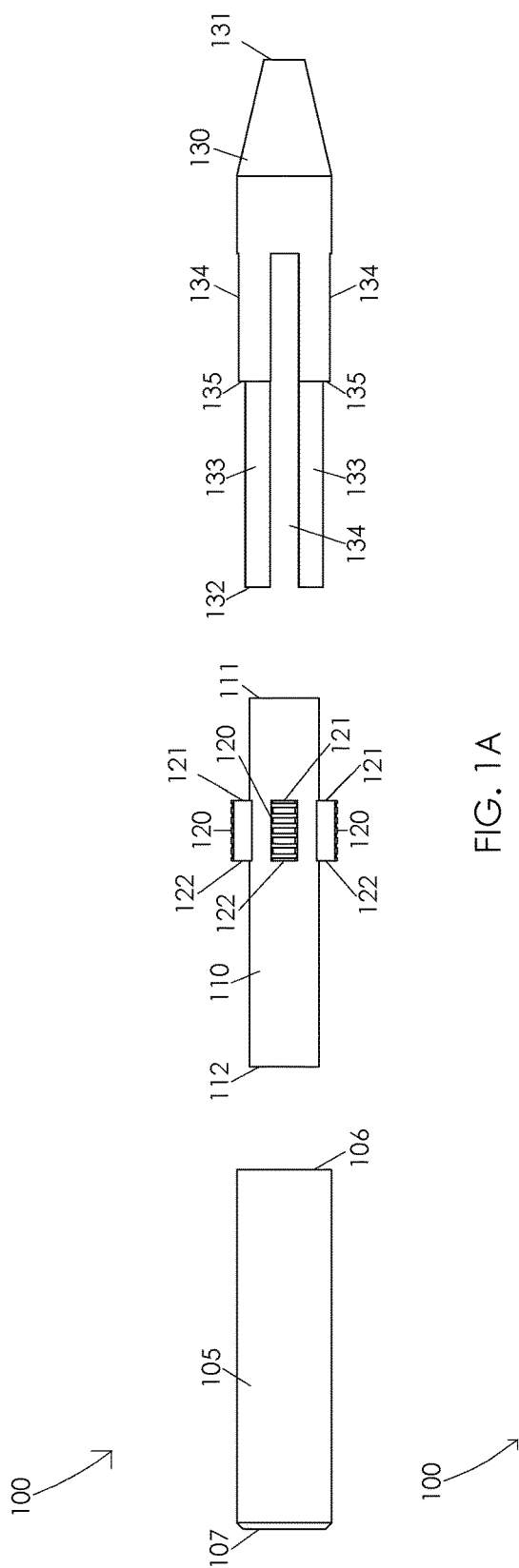
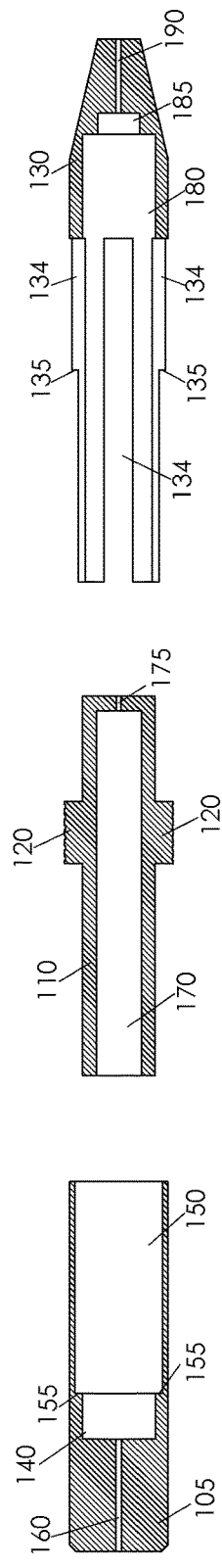
FIG. 1A
FIG. 1B

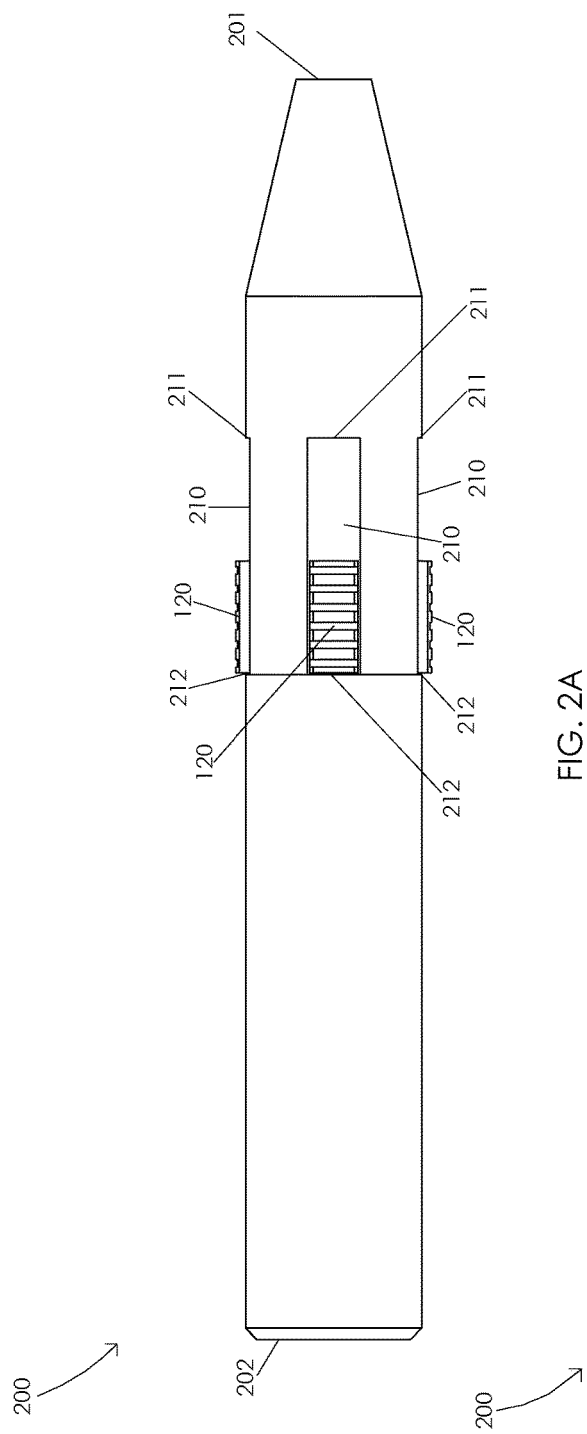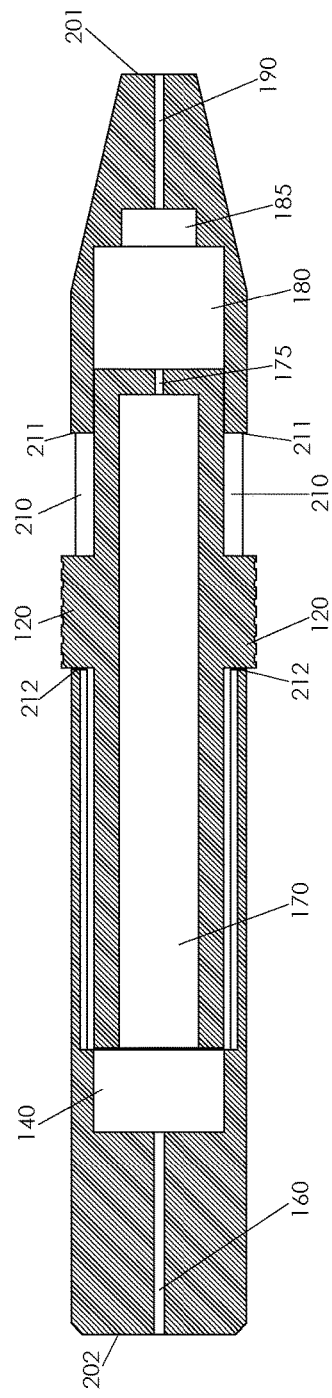

STEERABLE LASER PROBE

CROSS-REFERENCE TO RELATED APPLICATIONS

This application is a continuation of prior application Ser. No. 13/938,635, filed Jul. 10, 2013, which issued as U.S. Pat. No. 9,770,296 on Sep. 26, 2017, which claims the benefit of U.S. Provisional Application No. 61/677,665, filed Jul. 31, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle having a handle distal end and a handle proximal end, a plurality of actuation controls of the handle, a flexible housing tube having a flexible housing tube distal end and a flexible housing tube proximal end, and an optic fiber disposed within an inner bore of the handle and the flexible housing tube. Illustratively, an actuation of an actuation control of the plurality of actuation controls may be configured to gradually curve the flexible housing tube. In one or more embodiments, a gradual curving of the flexible housing tube may be configured to gradually curve the optic fiber. Illustratively, an actuation of an actuation control of the plurality of actuation controls may be configured to gradually straighten the flexible housing tube. In one or more embodiments, a gradual straightening of the flexible housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating an exploded view of a handle assembly;

FIGS. 2A and 2B are schematic diagrams illustrating a handle;

DETAILED DESCRIPTION OF AN ILLUSTRATIVE EMBODIMENT

Figure 3:
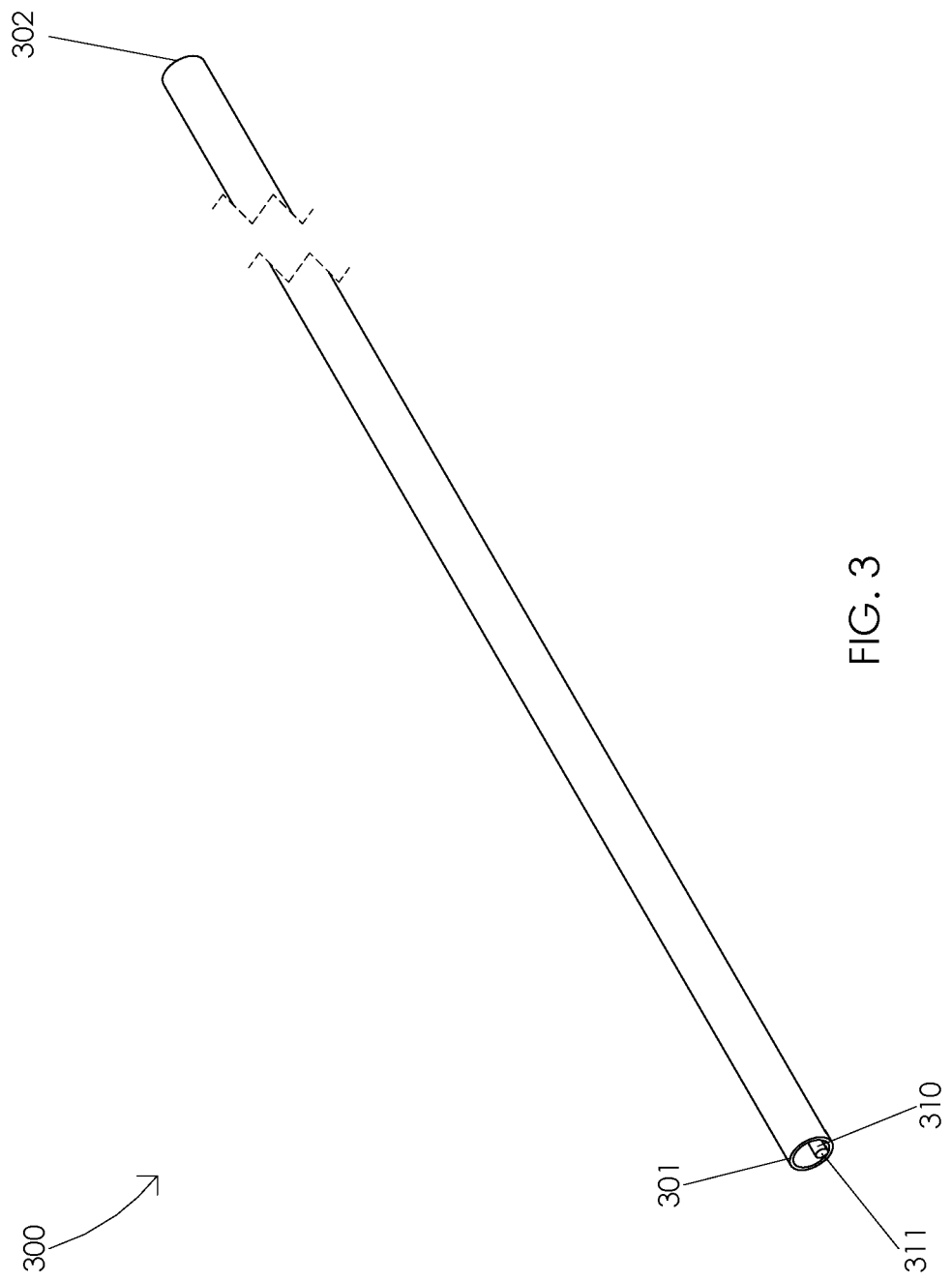
FIG. 3 is a schematic diagram illustrating a flexible housing tube.

FIGS. 1A and 1B are schematic diagrams illustrating an exploded view of a handle assembly 100. FIG. 1A illustrates a side view of handle assembly 100. In one or more embodiments, handle assembly 100 may comprise a handle end cap 105 having a handle end cap distal end 106 and a handle end cap proximal end 107, an actuation mechanism 110 having an actuation mechanism distal end 111 and an actuation mechanism proximal end 112, and a handle base 130 having a handle base distal end 131 and a handle base proximal end 132. Illustratively, actuation mechanism 110 may comprise a plurality of actuation controls 120. For example, each actuation control 120 of a plurality of actuation controls 120 may comprise an actuation control distal end 121 and an actuation control proximal end 122. In one or more embodiments, handle base 130 may comprise a plurality of handle base limbs 133, a plurality of handle base channels 134, and a handle end cap interface 135.

FIG. 1B illustrates a cross-sectional view of handle assembly 100. In one or more embodiments, handle assembly 100 may comprise a proximal chamber 140, a handle base housing 150, a handle base interface 155, an optic fiber housing 160, an inner bore 170, a flexible housing tube housing 175, an actuation mechanism guide 180, a pressure mechanism housing 185, and a flexible housing tube guide 190. Handle end cap 105, actuation mechanism 110, actuation control 120, and handle base 130 may be manufactured from any suitable material, e.g., polymers, metals, metal alloys, etc., or from any combination of suitable materials.

FIGS. 2A and 2B are schematic diagrams illustrating a handle 200. FIG. 2A illustrates a side view of handle 200. In one or more embodiments, handle 200 may comprise a handle distal end 201, a handle proximal end 202, and a plurality of actuation control guides 210. For example, each actuation control guide 210 of a plurality of actuation control guides 210 may comprise an actuation control guide distal end 211 and an actuation control guide proximal end 212. Illustratively, handle distal end 201 may comprise handle base distal end 131. In one or more embodiments, handle proximal end 202 may comprise handle end cap proximal end 107.

FIG. 2B illustrates a cross-sectional view of handle 200. Illustratively, actuation mechanism 110 may be disposed within handle end cap 105 and handle base 130. In one or more embodiments, a portion of actuation mechanism 110 may be disposed within handle base housing 150, e.g., actuation mechanism proximal end 112 may be disposed within handle base housing 150. Illustratively, a portion of actuation mechanism 110 may be disposed within actuation mechanism guide 180, e.g., actuation mechanism distal end 111 may be disposed within actuation mechanism guide 180. In one or more embodiments, a portion of handle base 130 may be disposed within handle end cap 105, e.g., handle base proximal end 132 may be disposed within handle end cap 105. Illustratively, a portion of handle base 130 may be disposed within handle base housing 150. In one or more embodiments, a portion of handle base 130 may be disposed within handle base housing 150, e.g., handle base proximal end 132 may be configured to interface with handle base interface 155. Illustratively, a portion of handle base 130 may be disposed within handle base housing 150, e.g., handle end cap distal end 106 may be configured to interface with handle end cap interface 135. In one or more embodiments, a portion of handle base 130 may be fixed within a portion of handle end cap 105, e.g., by an adhesive or any suitable fixation means. For example, a portion of handle base 130 may be fixed within handle base housing 150, e.g., by an adhesive or any suitable fixation means.

Illustratively, each actuation control 120 of a plurality of actuation controls 120 may be disposed within an actuation control guide 210 of a plurality of actuation control guides 210. In one or more embodiments, each actuation control guide 210 of a plurality of actuation control guides 210 may comprise a handle base channel 134 of a plurality of handle base channels 134. In one or more embodiments, at least one actuation control 120 may be configured to actuate within at least one actuation control guide 210. Illustratively, each actuation control 120 of a plurality of actuation controls 120 may be configured to actuate within an actuation control guide 210 of a plurality of actuation control guides 210. In one or more embodiments, an actuation of a particular actuation control 120 in a particular actuation control guide 210 may be configured to actuate each actuation control 120 of a plurality of actuation controls 120. In one or more embodiments, actuation controls 120 may be configured to actuate within actuation control guides 210 in pairs or groups. Illustratively, an actuation of first actuation control 120 within a first actuation control guide 210 may be configured to actuate a second actuation control 120 within a second actuation control guide 210.

In one or more embodiments, actuation mechanism 110 may be configured to actuate within actuation mechanism guide 180. For example, actuation mechanism guide 180 may comprise a lubricant configured to facilitate an actuation of actuation mechanism 110 within actuation mechanism guide 180. Illustratively, an actuation of an actuation control 120 within an actuation control guide 210 may be configured to actuate actuation mechanism 110, e.g., within actuation mechanism guide 180. In one or more embodiments, an actuation of an actuation control 120 towards an actuation control guide distal end 211, e.g., and away from an actuation control guide proximal end 212, may be configured to actuate actuation mechanism 110 towards handle distal end 201, e.g., and away from handle proximal end 202. Illustratively, an actuation of an actuation control 120 towards an actuation control guide proximal end 212, e.g., and away from an actuation control guide distal end 211, may be configured to actuate actuation mechanism towards handle proximal end 202, e.g., and away from handle distal end 201.

In one or more embodiments, a surgeon may actuate actuation mechanism 110 within actuation mechanism guide 180, e.g., by manipulating an actuation control 120 of a plurality of actuation controls 120 when handle 200 is in a first rotational orientation. Illustratively, the surgeon may rotate handle 200 and actuate actuation mechanism 110 within actuation mechanism guide 180, e.g., by manipulating an actuation control 120 of a plurality of actuation controls 120 when handle 200 is in a second rotational orientation. In one or more embodiments, the surgeon may rotate handle 200 and actuate actuation mechanism 110 within actuation mechanism guide 180, e.g., by manipulating an actuation control 120 of a plurality of actuation controls 120 when handle 200 is in a third rotational orientation. Illustratively, a surgeon may actuate actuation mechanism 110 within actuation mechanism guide 180, e.g., by manipulating an actuation control 120 of a plurality of actuation controls 120 when handle 200 is in any rotational orientation of a plurality of rotational orientations.

FIG. 3 is a schematic diagram illustrating a flexible housing tube 300. Illustratively, flexible housing tube 300 may comprise a flexible housing tube distal end 301 and a flexible housing tube proximal end 302. Flexible housing tube 300 may be manufactured from any suitable material, e.g., polymers, metals, metal alloys, etc., or from any combination of suitable materials. Illustratively, flexible housing tube 300 may comprise a shape memory material, e.g., Nitinol. In one or more embodiments, flexible housing tube 300 may be manufactured from a material having an ultimate tensile strength between 700 and 1000 MPa. Illustratively, flexible housing tube 300 may be manufactured from a material having ultimate tensile strength less than 700 MPa or greater than 1000 MPa. In one or more embodiments, flexible housing tube 300 may be manufactured from a material having a modulus of elasticity between 30 and 80 GPa. Illustratively, flexible housing tube 300 may be manufactured from a material having a modulus of elasticity less than 30 GPa or greater than 80 GPa.

In one or more embodiments, flexible housing tube 300 may be manufactured with dimensions suitable for performing microsurgical procedures, e.g., ophthalmic surgical procedures. Illustratively, flexible housing tube 300 may be manufactured at gauge sizes commonly used in ophthalmic surgical procedures, e.g., 23 gauge, 25 gauge, etc. In one or more embodiments, flexible housing tube 300 may be configured to be inserted in a cannula, e.g., a cannula used during an ophthalmic surgical procedure. For example, one or more properties of flexible housing tube 300 may be optimized to reduce friction as flexible housing tube 300 is inserted into a cannula. In one or more embodiments, one or more properties of flexible housing tube 300 may be optimized to reduce friction as flexible housing tube 300 is removed from a cannula. Illustratively, flexible housing tube 300 may have an ultimate tensile strength between 1000 MPa and 1100 MPa. In one or more embodiments, flexible housing tube 300 may have an ultimate tensile strength less than 1000 MPa or greater than 1100 MPa.

In one or more embodiments, an optic fiber 310 may be disposed within flexible housing tube 300. Illustratively, optic fiber 310 may comprise an optic fiber distal end 311 and an optic fiber proximal end 312. In one or more embodiments, optic fiber 310 may be configured to transmit light, e.g., laser light. Illustratively, optic fiber 310 may be disposed within flexible housing tube 300 wherein optic fiber distal end 311 may be adjacent to flexible housing tube distal end 301. In one or more embodiments, a portion of optic fiber 310 may be fixed to a portion of flexible housing tube 300, e.g., by an adhesive or any suitable fixation means.

Figure 4:
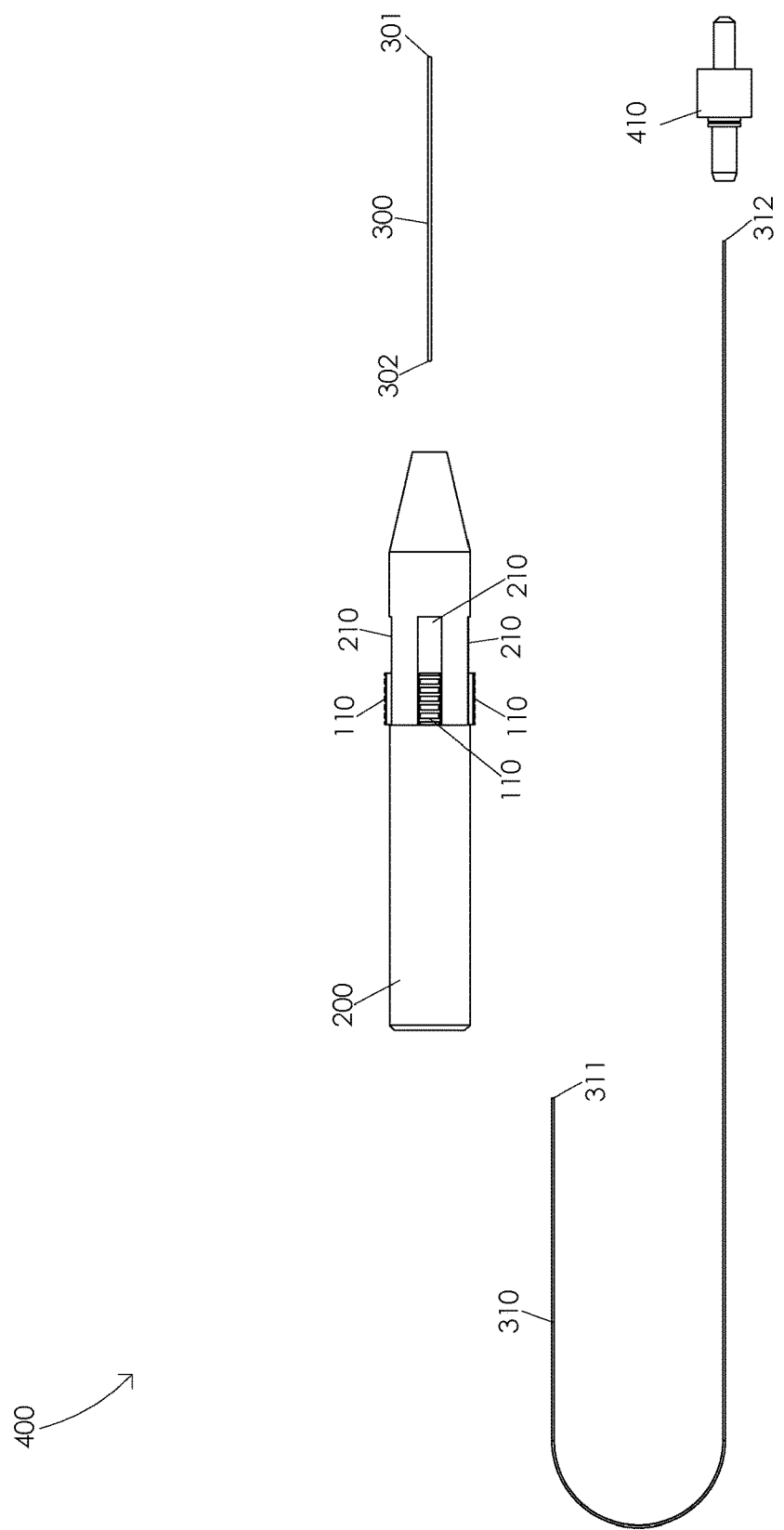
FIG. 4 is a schematic diagram illustrating an exploded view of a steerable laser probe assembly.

FIG. 4 is a schematic diagram illustrating an exploded view of a steerable laser probe assembly 400. In one or more embodiments, steerable laser probe assembly 400 may comprise a handle 200, a flexible housing tube 300 having a flexible housing tube distal end 301 and a flexible housing tube proximal end 302, an optic fiber 310 having an optic fiber distal end 311 and an optic fiber proximal end 312, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of flexible housing tube 300 may be fixed to actuation mechanism 110, e.g., flexible housing tube proximal end 302 may be fixed to actuation mechanism distal end 111. In one or more embodiments, a portion of flexible housing tube 300 may be fixed to actuation mechanism 110, e.g., by an adhesive or any suitable fixation means. Illustratively, a portion of flexible housing tube 300 may be disposed within actuation mechanism 110, e.g., flexible housing tube proximal end 302 may be disposed within flexible housing tube housing 175. In one or more embodiments, a portion of flexible housing tube 300 may be fixed within flexible housing tube housing 175, e.g., by an adhesive or any suitable fixation means. Illustratively, flexible housing tube 300 may be disposed within actuation mechanism guide 180 and flexible housing tube guide 190. In one or more embodiments, a portion of flexible housing tube 300 may extend from handle distal end 201, e.g., flexible housing tube distal end 301 may extend from handle distal end 201.

Illustratively, optic fiber 310 may be disposed within optic fiber housing 160, proximal chamber 140, inner bore 170, flexible housing tube housing 175, flexible housing tube 300, actuation mechanism guide 180, and flexible housing tube guide 190. In one or more embodiments, a portion of optic fiber 310 may be fixed to a portion of flexible housing tube 300, e.g., by an adhesive or any suitable fixation means. Illustratively, a portion of optic fiber 310 may be fixed in a position relative to handle 200. In one or more embodiments, a portion of optic fiber 310 may be fixed within optic fiber housing 160, e.g., by an adhesive or any suitable fixation means. Illustratively, a portion of optic fiber 310 may be fixed within optic fiber housing 160, e.g., by a press fit or any suitable fixation means. In one or more embodiments, a portion of optic fiber 310 may be fixed to a portion of flexible housing tube 300 and a portion of optic fiber 310 may be fixed in a position relative to handle 200.

Illustratively, an actuation of an actuation control 120 within an actuation control guide 210, e.g., towards actuation control guide distal end 211 and away from actuation control guide proximal end 212, may be configured to actuate actuation mechanism 110 within actuation mechanism guide 180, e.g., towards handle distal end 201 and away from handle proximal end 202. In one or more embodiments, an actuation of actuation mechanism 110 towards handle distal end 201 and away from handle proximal end 202 may be configured to extend actuation mechanism 110 relative to optic fiber 310. Illustratively, an extension of actuation mechanism 110 relative to optic fiber 310 may be configured to extend flexible housing tube 300 relative to optic fiber 310. In one or more embodiments, optic fiber 310 may be configured to resist an extension of flexible housing tube 300 relative to optic fiber 310. Illustratively, optic fiber 310 may be configured to resist an extension of flexible housing tube 300 relative to optic fiber 310, e.g., a portion of optic fiber 310 may be configured to apply a force to a portion of flexible housing tube 300. In one or more embodiments, an application of a force, e.g., a resistive force, to a portion of flexible housing tube 300 may be configured to compress a portion of flexible housing tube 300 causing flexible housing tube 300 to gradually curve. Illustratively, a gradual curving of flexible housing tube 300 may be configured to gradually curve optic fiber 310. In one or more embodiments, an actuation of an actuation control 120 within an actuation control guide 210, e.g., towards actuation control guide distal end 211 and away from actuation control guide proximal end 212, may be configured to gradually curve optic fiber 310.

Illustratively, an actuation of an actuation control 120 within an actuation control guide 210, e.g., towards actuation control guide proximal end 212 and away from actuation control guide distal end 211, may be configured to actuate actuation mechanism 110 within actuation mechanism guide 180, e.g., towards handle proximal end 202 and away from handle distal end 201. In one or more embodiments, an actuation of actuation mechanism 110 towards handle proximal end 202 and away from handle distal end 201 may be configured to retract actuation mechanism 110 relative to optic fiber 310. Illustratively, a retraction of actuation mechanism 110 relative to optic fiber 310 may be configured to retract flexible housing tube 300 relative to optic fiber 310. In one or more embodiments, optic fiber 310 may be configured to facilitate a retraction of flexible housing tube 300 relative to optic fiber 310. Illustratively, optic fiber 310 may be configured to facilitate a retraction of flexible housing tube 300 relative to optic fiber 310, e.g., a portion of optic fiber 310 may be configured to reduce a force applied to a portion of flexible housing tube 300. In one or more embodiments, a reduction of a force, e.g., a resistive force, applied to a portion of flexible housing tube 300 may be configured to decompress a portion of flexible housing tube 300 causing flexible housing tube 300 to gradually straighten. Illustratively, a gradual straightening of flexible housing tube 300 may be configured to gradually straighten optic fiber 310. In one or more embodiments, an actuation of an actuation control 120 within an actuation control guide 210, e.g., towards actuation control guide proximal end 212 and away from actuation control guide distal end 211, may be configured to gradually straighten optic fiber 310.

Figure 5A:
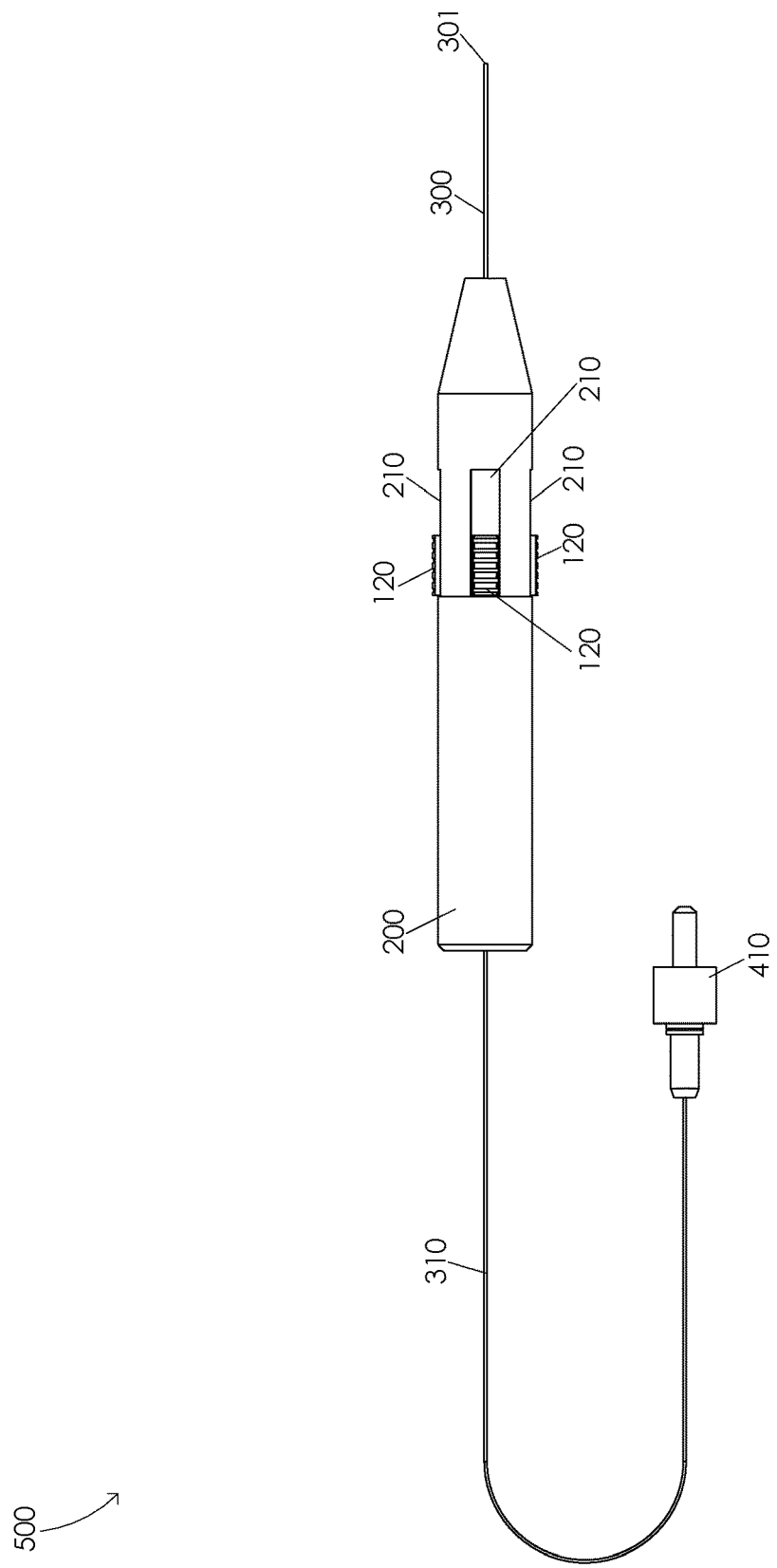
FIGS. 5A, 5B, 5C, 5D, and 5E are schematic diagrams illustrating a gradual curving of an optic fiber.

FIGS. 5A, 5B, 5C, 5D, and 5E are schematic diagrams illustrating a gradual curving of an optic fiber 310. FIG. 5A illustrates a straight optic fiber 500. In one or more embodiments, optic fiber 310 may comprise a straight optic fiber 500, e.g., when flexible housing tube 300 is fully retracted relative to handle proximal end 202. Illustratively, optic fiber 310 may comprise a straight optic fiber 500, e.g., when an actuation control 120 of a plurality of actuation controls 120 is fully retracted relative to an actuation control guide proximal end 212. In one or more embodiments, optic fiber 310 may comprise a straight optic fiber 500, e.g., when actuation mechanism 110 is fully retracted relative to handle proximal end 202. Illustratively, a line tangent to optic fiber distal end 311 may be parallel to a line tangent to flexible housing tube proximal end 302, e.g., when optic fiber 310 comprises a straight optic fiber 500.

Figure 5B:
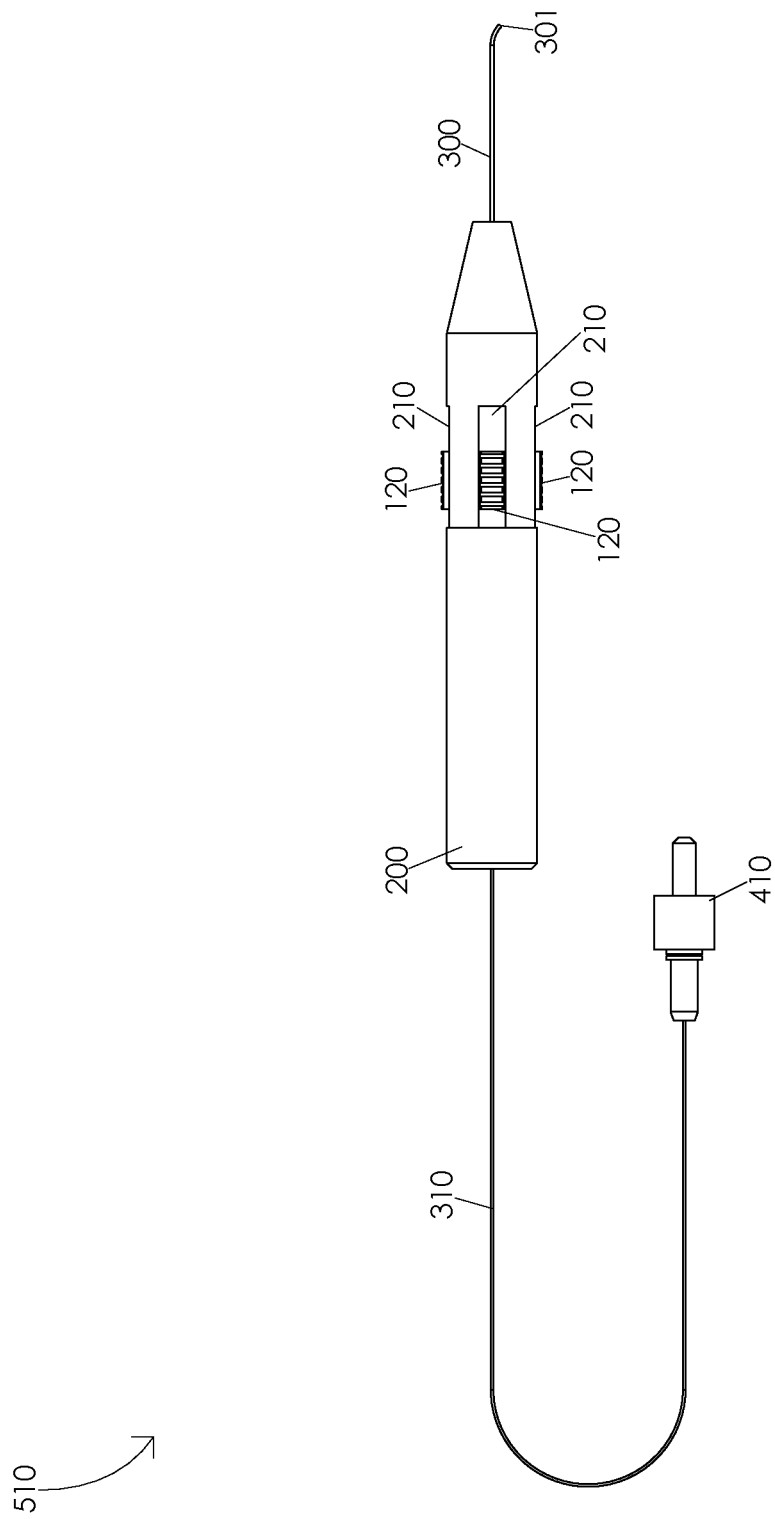

FIG. 5B illustrates an optic fiber in a first curved position 510. In one or more embodiments, an actuation of an actuation control 120 within an actuation control guide 210, e.g., towards actuation control guide distal end 211 and away from actuation control guide proximal end 212, may be configured to gradually curve optic fiber 310 from a straight optic fiber 500 to an optic fiber in a first curved position 510. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend flexible housing tube 300 relative to optic fiber 310. Illustratively, a portion of optic fiber 310, e.g., a portion of optic fiber 310 fixed to a portion of flexible housing tube 300, may be configured to resist an extension of flexible housing tube 300 relative to optic fiber 310. In one or more embodiments, an extension of flexible housing tube 300 relative to optic fiber 310 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from a straight optic fiber 500 to an optic fiber in a first curved position 510. In one or more embodiments, a line tangent to optic fiber distal end 311 may intersect a line tangent to flexible housing tube proximal end 302 at a first angle, e.g., when optic fiber 310 comprises an optic fiber in a first curved position 510. Illustratively, the first angle may comprise any angle greater than zero degrees. For example, the first angle may comprise a 45 degree angle.

Figure 5C:
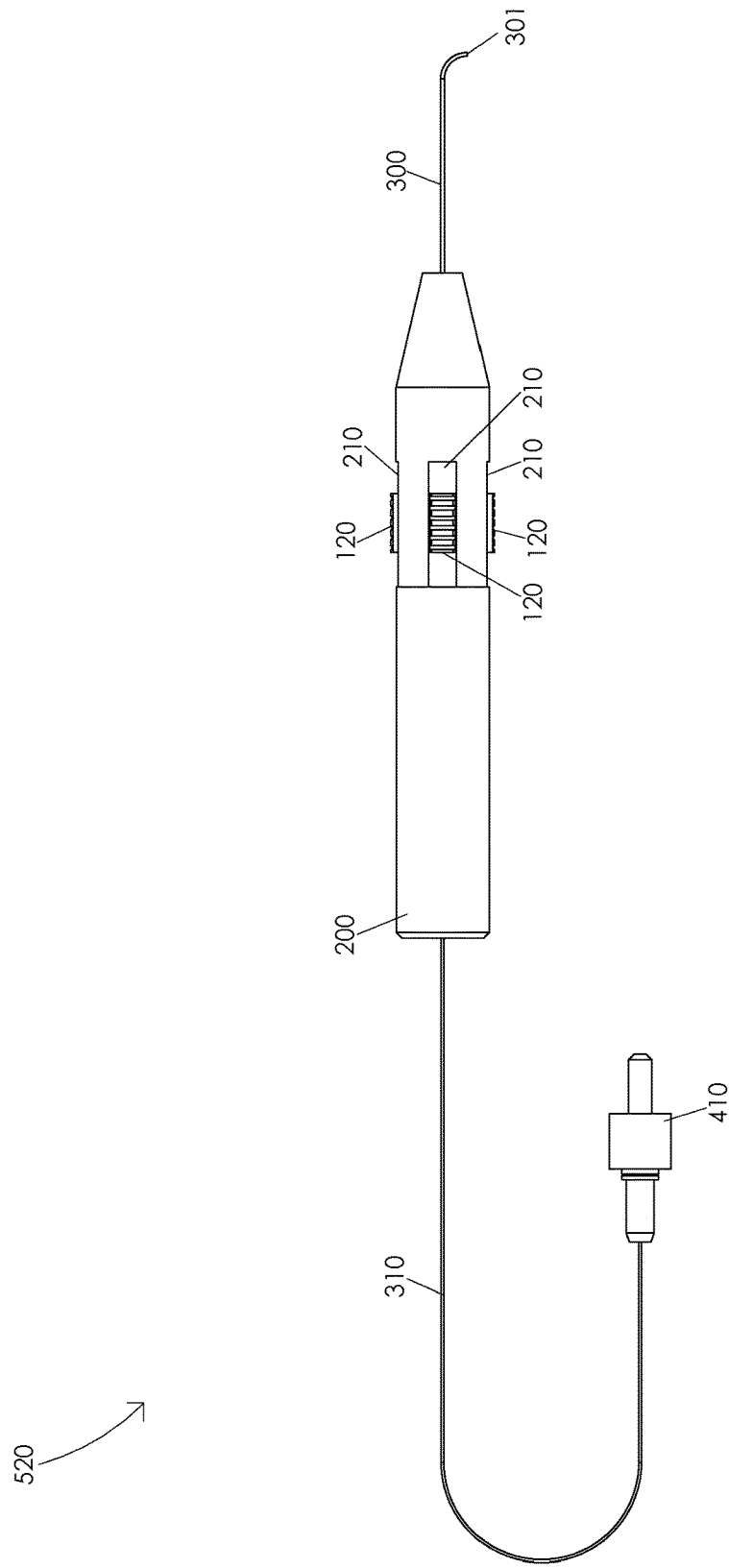

FIG. 5C illustrates an optic fiber in a second curved position 520. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a first curved position 510 to an optic fiber in a second curved position 520. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend flexible housing tube 300 relative to optic fiber 310. Illustratively, a portion of optic fiber 310, e.g., a portion of optic fiber 310 fixed to a portion of flexible housing tube 300, may be configured to resist an extension of flexible housing tube 300 relative to optic fiber 310. In one or more embodiments, an extension of flexible housing tube 300 relative to optic fiber 310 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a first curved position 510 to an optic fiber in a second curved position 520. In one or more embodiments, a line tangent to optic fiber distal end 311 may intersect a line tangent to flexible housing tube proximal end 302 at a second angle, e.g., when optic fiber 310 comprises an optic fiber in a second curved position 520. Illustratively, the second angle may comprise any angle greater than the first angle. For example, the second angle may comprise a 90 degree angle.

Figure 5D:
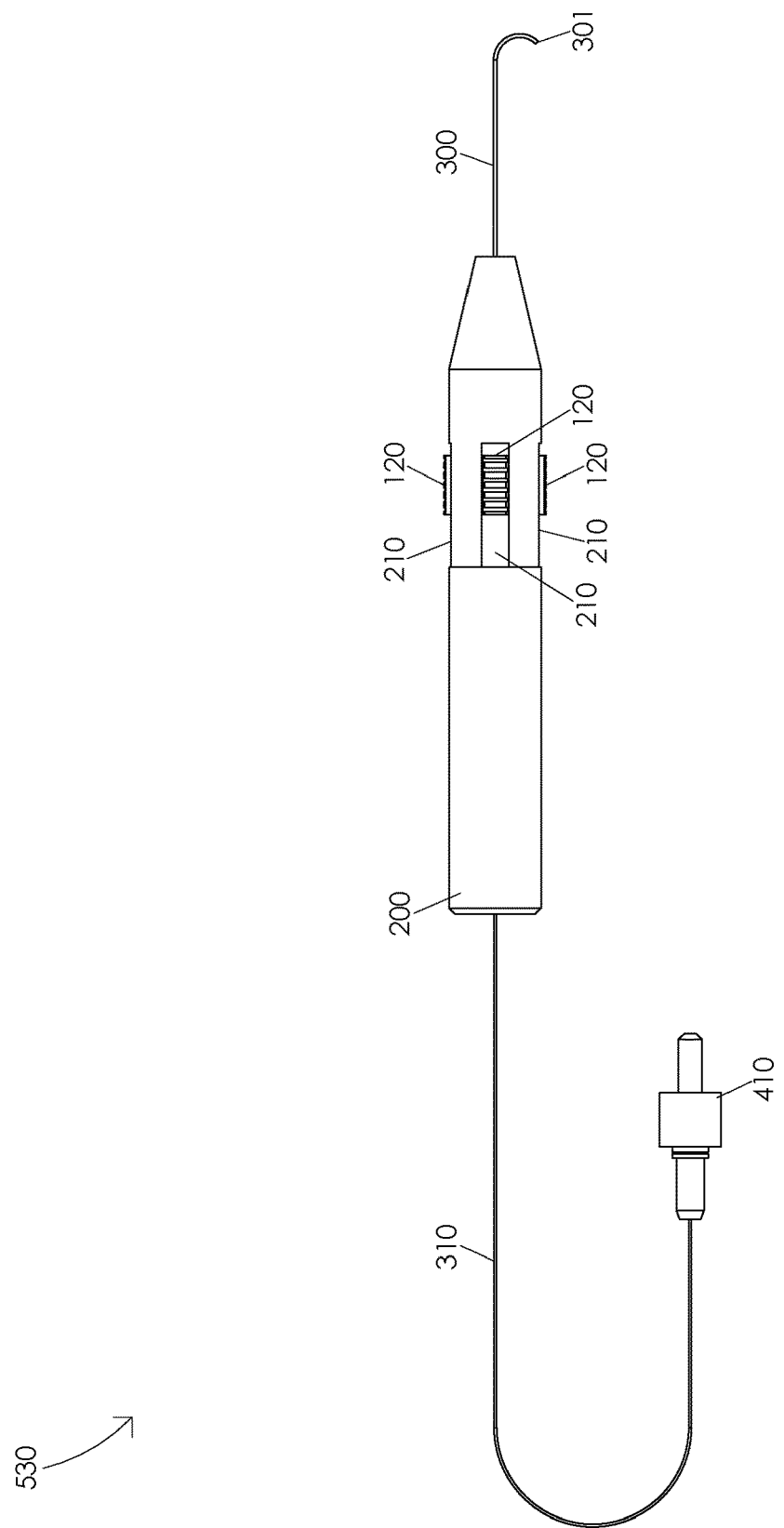

FIG. 5D illustrates an optic fiber in a third curved position 530. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a second curved position 520 to an optic fiber in a third curved position 530. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend flexible housing tube 300 relative to optic fiber 310. Illustratively, a portion of optic fiber 310, e.g., a portion of optic fiber 310 fixed to a portion of flexible housing tube 300, may be configured to resist an extension of flexible housing tube 300 relative to optic fiber 310. In one or more embodiments, an extension of flexible housing tube 300 relative to optic fiber 310 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a second curved position 520 to an optic fiber in a third curved position 530. In one or more embodiments, a line tangent to optic fiber distal end 311 may intersect a line tangent to flexible housing tube proximal end 302 at a third angle, e.g., when optic fiber 310 comprises an optic fiber in a third curved position 530. Illustratively, the third angle may comprise any angle greater than the second angle. For example, the third angle may comprise a 135 degree angle.

Figure 5E:
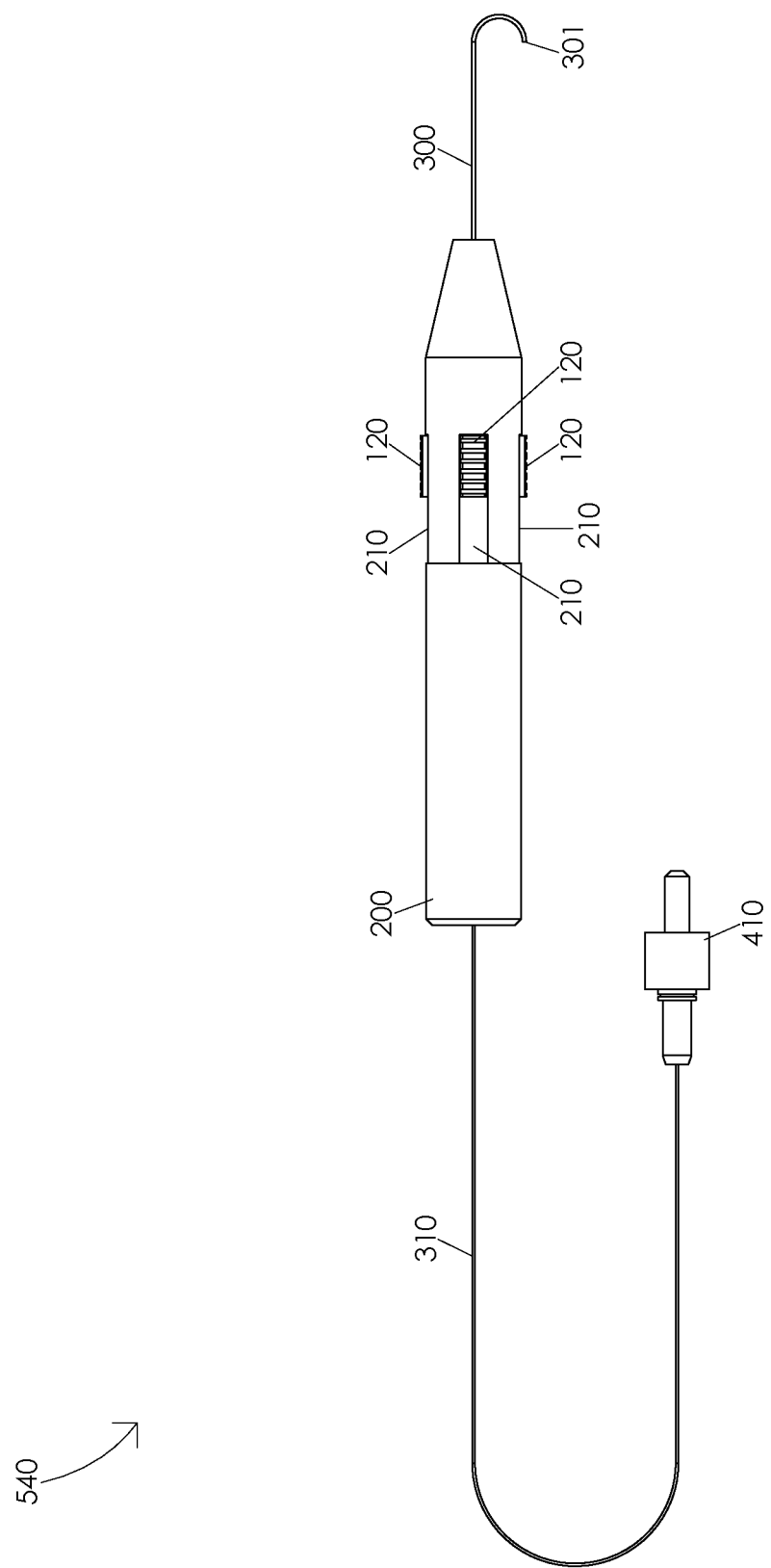

FIG. 5E illustrates an optic fiber in a fourth curved position 540. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a third curved position 530 to an optic fiber in a fourth curved position 540. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend flexible housing tube 300 relative to optic fiber 310. Illustratively, a portion of optic fiber 310, e.g., a portion of optic fiber 310 fixed to a portion of flexible housing tube 300, may be configured to resist an extension of flexible housing tube 300 relative to optic fiber 310. In one or more embodiments, an extension of flexible housing tube 300 relative to optic fiber 310 may be configured to apply a force to a portion of flexible housing tube 300.

Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a third curved position 530 to an optic fiber in a fourth curved position 540. In one or more embodiments, a line tangent to optic fiber distal end 311 may be parallel to a line tangent to flexible housing tube proximal end 302, e.g., when optic fiber 310 comprises an optic fiber in a fourth curved position 540.

In one or more embodiments, one or more properties of a steerable laser probe may be adjusted to attain one or more desired steerable laser probe features. Illustratively, a length that flexible housing tube distal end 301 extends from actuation mechanism distal end 111 may be adjusted to vary an amount of actuation of an actuation control 120 of a plurality of actuation controls 120 configured to curve flexible housing tube 300 to a particular curved position. In one or more embodiments, a stiffness of flexible housing tube 300 may be adjusted to vary an amount of actuation of an actuation control 120 of a plurality of actuation controls 120 configured to curve flexible housing tube 300 to a particular curved position. Illustratively, flexible housing tube 300 may comprise a solid tube structure. In one or more embodiments, flexible housing tube 300 may comprise one or more apertures, e.g., configured to vary a stiffness of flexible housing tube 300. Illustratively, a material comprising flexible housing tube 300 may be adjusted to vary an amount of actuation of an actuation control 120 of a plurality of actuation controls 120 configured to curve flexible housing tube 300 to a particular curved position. In one or more embodiments, a stiffness of flexible housing tube 300 may be adjusted to vary a bend radius of flexible housing tube 300. Illustratively, a stiffness of flexible housing tube 300 may be adjusted to vary a radius of curvature of flexible housing tube 300, e.g., when flexible housing tube 300 is in a particular curved position.

In one or more embodiments, a geometry of actuation mechanism 110 may be adjusted to vary an amount of actuation of an actuation control 120 of a plurality of actuation controls 120 configured to curve flexible housing tube 300 to a particular curved position. Illustratively, a geometry of actuation mechanism guide 180 may be adjusted to vary an amount of actuation of an actuation control 120 of a plurality of actuation controls 120 configured to curve flexible housing tube 300 to a particular curved position. In one or more embodiments, a geometry of handle end cap 105 or a geometry of handle base 130 may be adjusted to vary an amount of actuation of an actuation control 120 of a plurality of actuation controls 120 configured to curve flexible housing tube 300 to a particular curved position. Illustratively, one or more locations within flexible housing tube 300 wherein optic fiber 310 may be fixed to a portion of flexible housing tube 300 may be adjusted to vary an amount of actuation of an actuation control 120 of a plurality of actuation controls 120 configured to curve flexible housing tube 300 to a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, an optic fiber sleeve may be configured to compress a portion of flexible housing tube 300. For example, an optic fiber sleeve may enclose a portion of optic fiber 310 and the optic fiber sleeve may be fixed in a position relative to handle base 200, e.g., the optic fiber sleeve may be fixed within optic fiber housing 160 by an adhesive or any suitable fixation means. Illustratively, a portion of the optic fiber sleeve may be fixed to a portion of flexible housing tube 300, e.g., by an adhesive or any suitable fixation means. In one or more embodiments, an actuation of an actuation control 120 of a plurality of actuation controls 120 may be configured to extend flexible housing tube 300 relative to an optic fiber sleeve. Illustratively, an extension of flexible housing tube 300 relative to an optic fiber sleeve may be configured to cause the optic fiber sleeve to apply a force, e.g., a compressive force, to a portion of flexible housing tube 300 causing flexible housing tube 300 to gradually curve. In one or more embodiments, a gradual curving of flexible housing tube 300 may be configured to gradually curve optic fiber 310.

Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to an actuation of an actuation control 120 of a plurality of actuation controls 120. In one or more embodiments, a portion of a steerable laser probe, e.g., handle 200, may be marked in a manner configured to indicate a direction that optic fiber 310 may curve. For example, a portion of flexible housing tube 300 may comprise a mark configured to indicate a direction that optic fiber 310 may curve. Illustratively, flexible housing tube 300 may comprise a slight curve, e.g., a curve less than 7.5 degrees, when an actuation control 120 of a plurality of actuation controls 120 is fully retracted relative to an actuation control guide proximal end 212. In one or more embodiments, flexible housing tube 300 may comprise a slight curve configured to indicate a direction that optic fiber 310 may curve, e.g., due to an extension of an actuation control 120 of a plurality of actuation controls 120 relative to an actuation control guide proximal end 212.

In one or more embodiments, a steerable laser probe may comprise a pressure mechanism configured to provide a force. Illustratively, a pressure mechanism may be disposed within pressure mechanism housing 185. For example, a pressure mechanism may be disposed within proximal chamber 140. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 110 relative to handle proximal end 202. Illustratively, a pressure mechanism may be configured to provide a facilitating force, e.g., to facilitate a retraction of actuation mechanism 110 relative to handle proximal end 202. In one or more embodiments, a pressure mechanism may be configured to provide a resistive force, e.g., to resist a retraction of actuation mechanism 110 relative to handle proximal end 202. Illustratively, a pressure mechanism may be configured to provide a facilitating force, e.g., to facilitate an extension of actuation mechanism 110 relative to handle proximal end 202. In one or more embodiments, a pressure mechanism may comprise a spring or a coil. Illustratively, a pressure mechanism may comprise a pneumatic system or any system configured to provide a force.

In one or more embodiments, one or more actuation controls 120 may be fixed together. For example, a first actuation control 120 may be connected to a second actuation control 120 wherein an actuation of the first actuation control 120 is configured to actuate the second actuation control 120 and an actuation of the second actuation control 120 is configured to actuate the first actuation control 120. Illustratively, each actuation control 120 of a plurality of actuation controls 120 may be connected wherein an actuation of a particular actuation control 120 is configured to actuate each actuation control 120 of the plurality of actuation controls 120. In one or more embodiments, each actuation control 120 may be connected to another actuation control 120 of a plurality of actuation controls 120, e.g., by a ring or any suitable structure wherein a surgeon may actuate each actuation control 120 of the plurality of actuation controls 120 in any rotational orientation of handle 200.

Figure 6A:
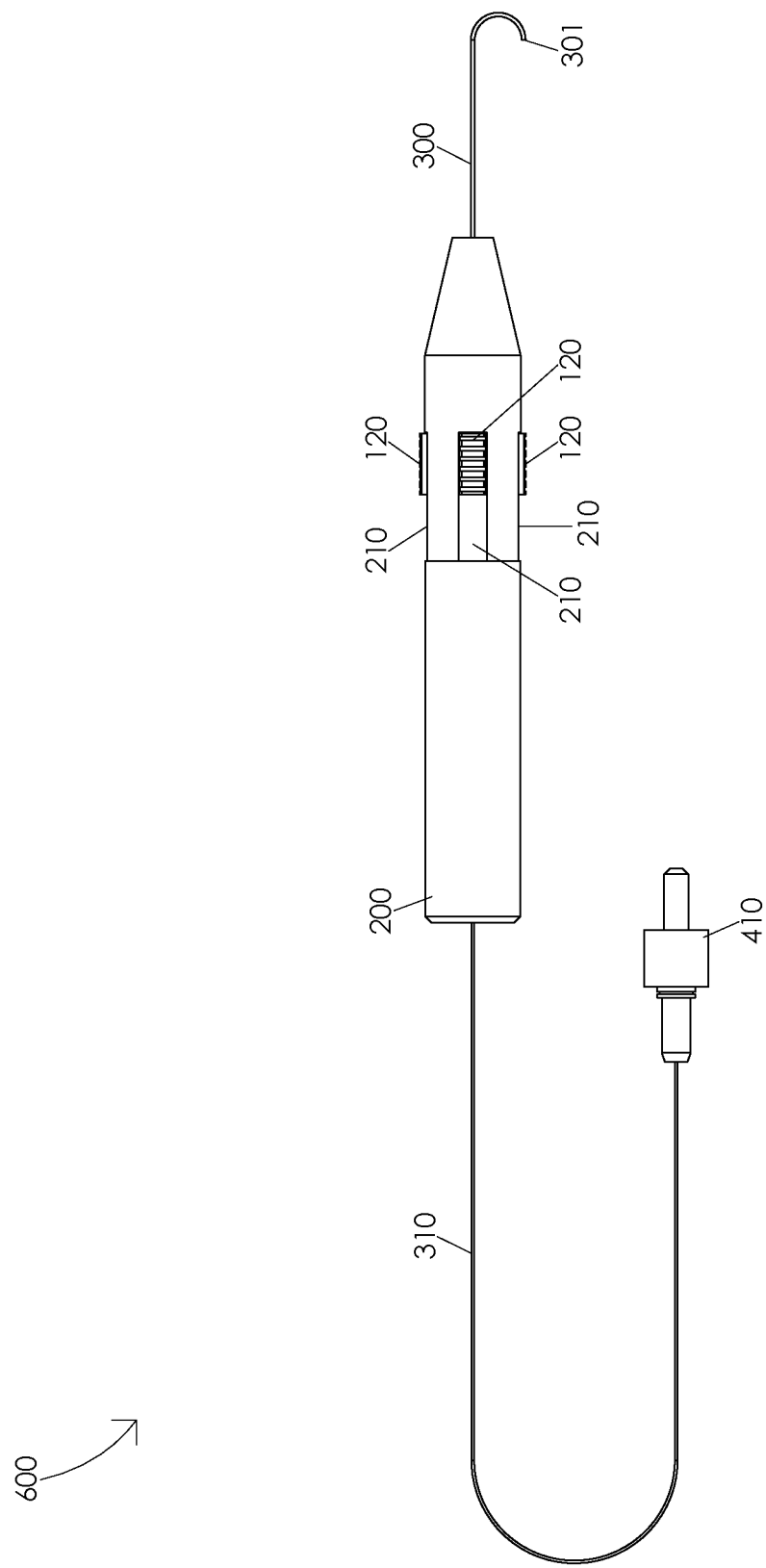
FIGS. 6A, 6B, 6C, 6D, and 6E are schematic diagrams illustrating a gradual straightening of an optic fiber.

FIGS. 6A, 6B, 6C, 6D, and 6E are schematic diagrams illustrating a gradual straightening of an optic fiber 310. FIG. 6A illustrates a fully curved optic fiber 600. In one or more embodiments, optic fiber 310 may comprise a fully curved optic fiber 600, e.g., when flexible housing tube 300 is fully extended relative to handle proximal end 202. Illustratively, optic fiber 310 may comprise a fully curved optic fiber 600, e.g., when an actuation control 120 of a plurality of actuation controls 120 is fully extended relative to an actuation control guide proximal end 212. In one or more embodiments, optic fiber 310 may comprise a fully curved optic fiber 600, e.g., when actuation mechanism 110 is fully extended relative to handle proximal end 202. Illustratively, a line tangent to optic fiber distal end 311 may be parallel to a line tangent to flexible housing tube proximal end 302, e.g., when optic fiber 310 comprises a fully curved optic fiber 600.

Figure 6B:
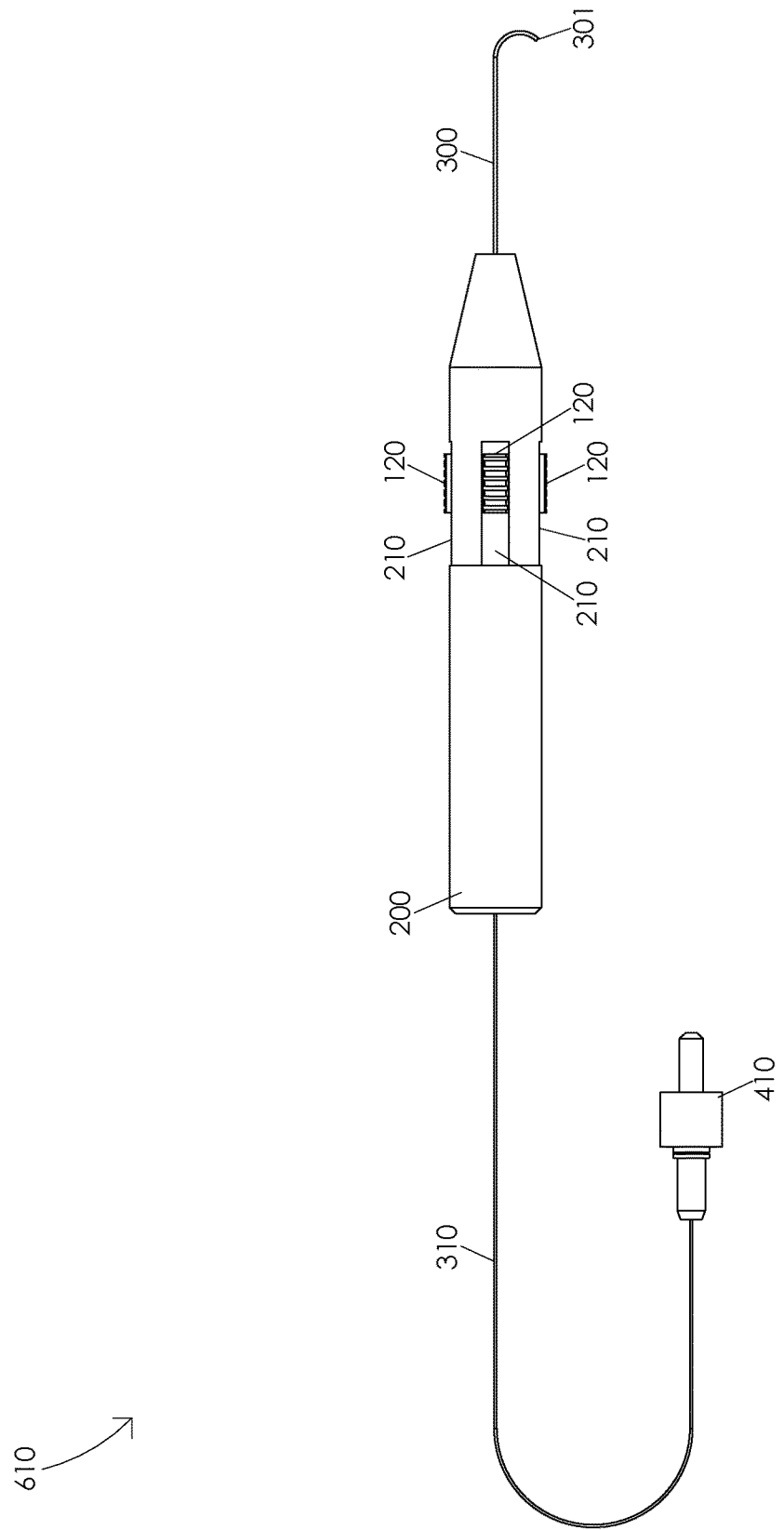

FIG. 6B illustrates an optic fiber in a first partially straightened position 610. In one or more embodiments, an actuation of an actuation control 120 within an actuation control guide 210, e.g., towards actuation control guide proximal end 212 and away from actuation control guide distal end 211, may be configured to gradually straighten optic fiber 310 from a fully curved optic fiber 600 to an optic fiber in a first partially straighten position 610. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract flexible housing tube 300 relative to optic fiber 310. Illustratively, a portion of optic fiber 310, e.g., a portion of optic fiber 310 fixed to a portion of flexible housing tube 300, may be configured to facilitate a retraction of flexible housing tube 300 relative to optic fiber 310. In one or more embodiments, a retraction of flexible housing tube 300 relative to optic fiber 310 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from a fully curved optic fiber 600 to an optic fiber in a first partially straightened position 610. In one or more embodiments, a line tangent to optic fiber distal end 311 may intersect a line tangent to flexible housing tube proximal end 302 at a first partially straightened angle, e.g., when optic fiber 310 comprises an optic fiber in a first partially straightened position 610. Illustratively, the first partially straightened angle may comprise any angle less than 180 degrees. For example, the first partially straightened angle may comprise a 135 degree angle.

Figure 6C:
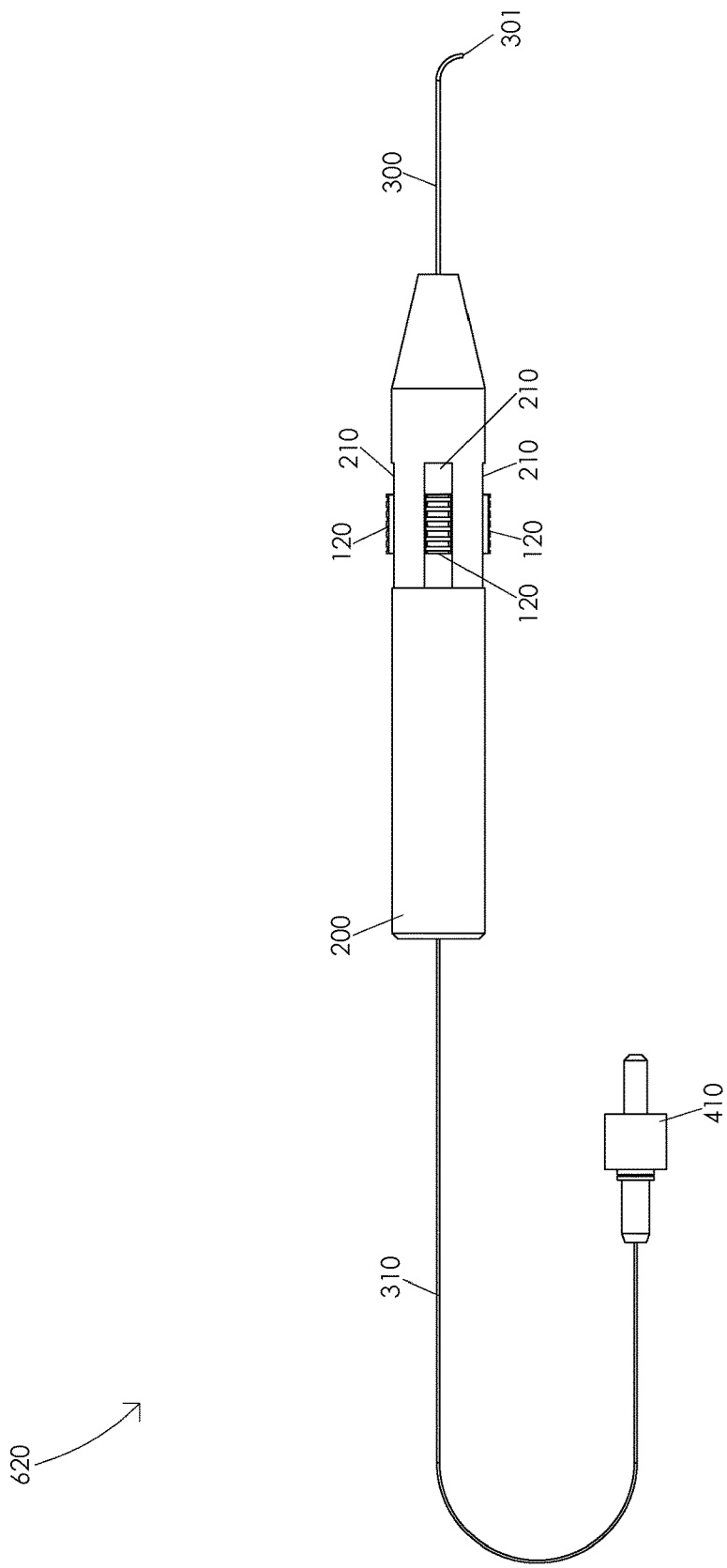

FIG. 6C illustrates an optic fiber in a second partially straightened position 620. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a first partially straighten position 610 to an optic fiber in a second partially straightened position 620. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract flexible housing tube 300 relative to optic fiber 310. Illustratively, a portion of optic fiber 310, e.g., a portion of optic fiber 310 fixed to a portion of flexible housing tube 300, may be configured to facilitate a retraction of flexible housing tube 300 relative to optic fiber 310. In one or more embodiments, a retraction of flexible housing tube 300 relative to optic fiber 310 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a first partially straightened position 610 to an optic fiber in a second partially straightened position 620. In one or more embodiments, a line tangent to optic fiber distal end 311 may intersect a line tangent to flexible housing tube proximal end 302 at a second partially straightened angle, e.g., when optic fiber 310 comprises an optic fiber in a second partially straightened position 620. Illustratively, the second partially straightened angle may comprise any angle less than the first partially straightened angle. For example, the second partially straightened angle may comprise a 90 degree angle.

Figure 6D:
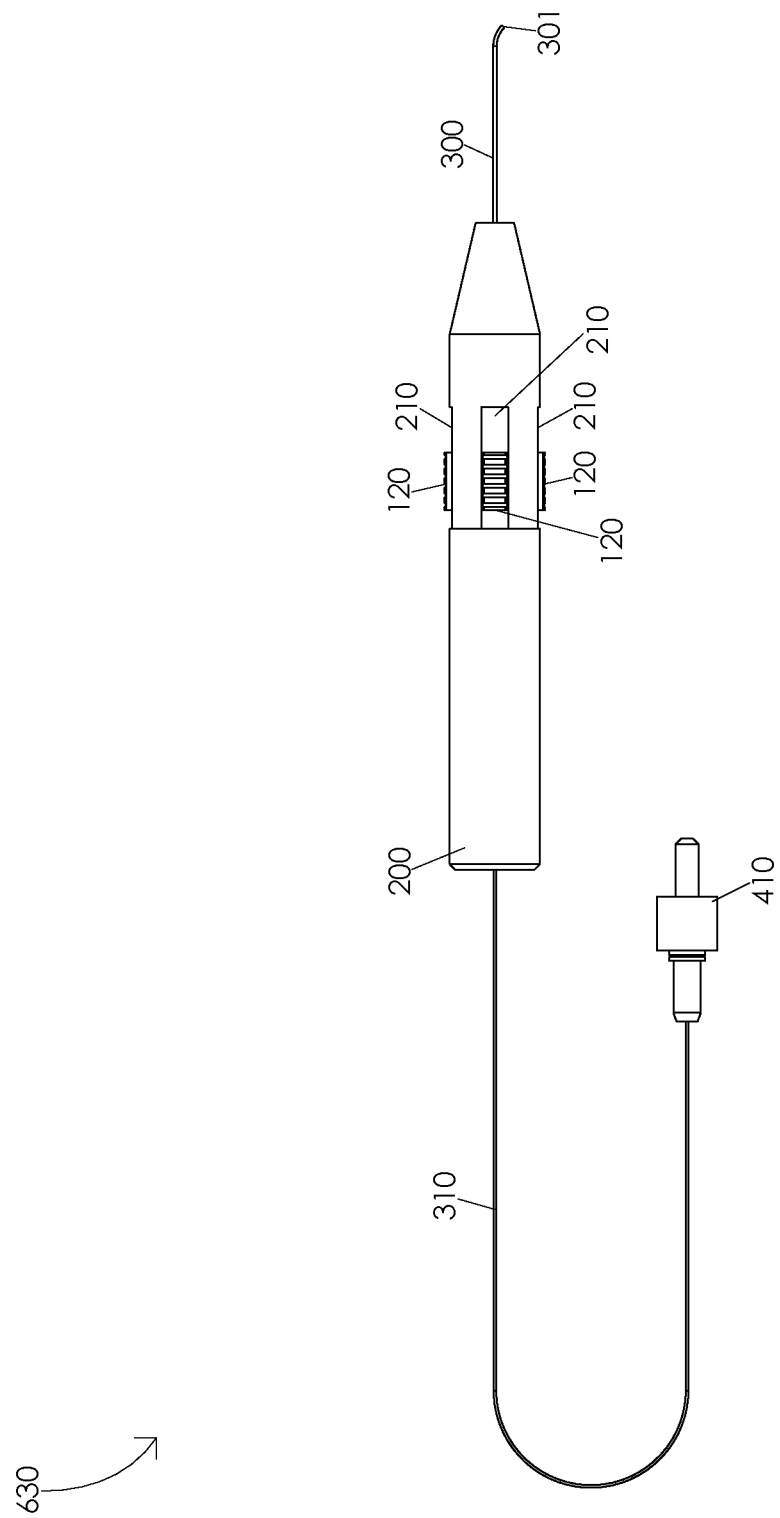

FIG. 6D illustrates an optic fiber in a third partially straightened position 630. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a second partially straightened position 620 to an optic fiber in a third partially straightened position 630. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract flexible housing tube 300 relative to optic fiber 310. Illustratively, a portion of optic fiber 310, e.g., a portion of optic fiber 310 fixed to a portion of flexible housing tube 300, may be configured to facilitate a retraction of flexible housing tube 300 relative to optic fiber 310. In one or more embodiments, a retraction of flexible housing tube 300 relative to optic fiber 310 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a second partially straightened position 620 to an optic fiber in a third partially straightened position 630. In one or more embodiments, a line tangent to optic fiber distal end 311 may intersect a line tangent to flexible housing tube proximal end 302 at a third partially straightened angle, e.g., when optic fiber 310 comprises an optic fiber in a third partially straightened position 630. Illustratively, the third partially straightened angle may comprise any angle less than the second partially straightened angle. For example, the third partially straightened angle may comprise a 45 degree angle.

Figure 6E:
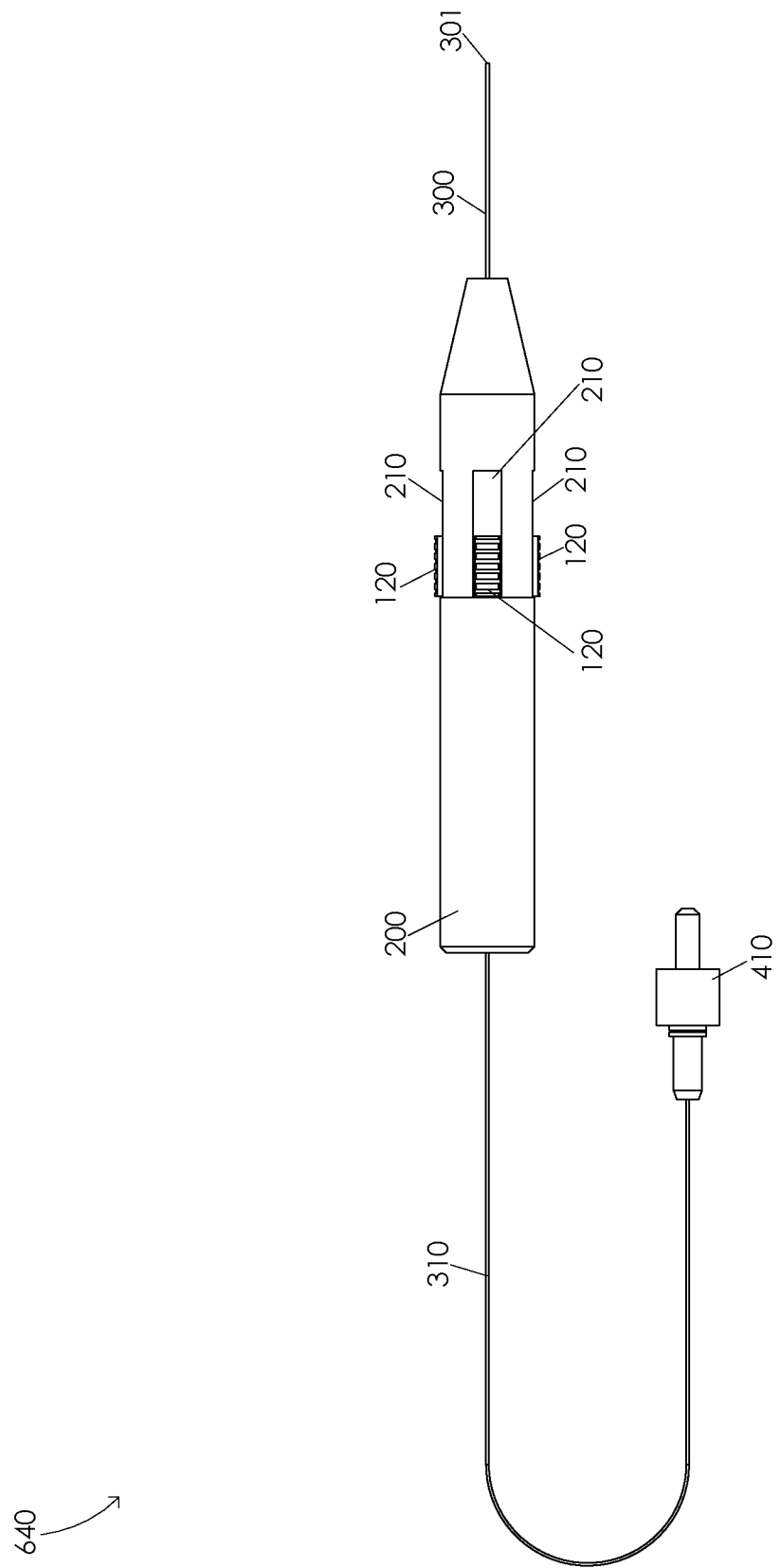

FIG. 6E illustrates an optic fiber in a fully straightened position 640. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a third partially straightened position 630 to an optic fiber in a fully straightened position 640. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract flexible housing tube 300 relative to optic fiber 310. Illustratively, a portion of optic fiber 310, e.g., a portion of optic fiber 310 fixed to a portion of flexible housing tube 300, may be configured to facilitate a retraction of flexible housing tube 300 relative to optic fiber 310. In one or more embodiments, a retraction of flexible housing tube 300 relative to optic fiber 310 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a third partially straightened position 630 to an optic fiber in a fully straightened position 640. In one or more embodiments, a line tangent to optic fiber distal end 311 may be parallel to a line tangent to flexible housing tube proximal end 302, e.g., when optic fiber 310 comprises an optic fiber in a fully straightened position 640.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 200 to orient flexible housing tube 300 in an orientation configured to cause a curvature of flexible housing tube 300 within the particular transverse plane of the inner eye and varying an amount of actuation of an actuation control 120 of a plurality of actuation controls 120. Illustratively, a surgeon may aim optic fiber distal end 311 at any target within a particular sagittal plane of the inner eye by, e.g., rotating handle 200 to orient flexible housing tube 300 in an orientation configured to cause a curvature of flexible housing tube 300 within the particular sagittal plane of the inner eye and varying an amount of actuation of an actuation control 120 of a plurality of actuation controls 120. In one or more embodiments, a surgeon may aim optic fiber distal end 311 at any target within a particular frontal plane of the inner eye by, e.g., varying an amount of actuation of an actuation control 120 of a plurality of actuation controls 120 to orient a line tangent to optic fiber distal end 311 wherein the line tangent to optic fiber distal end 311 is within the particular frontal plane of the inner eye and rotating handle 200. Illustratively, a surgeon may aim optic fiber distal end 311 at any target located outside of the particular transverse plane, the particular sagittal plane, and the particular frontal plane of the inner eye, e.g., by varying a rotational orientation of handle 200 and varying an amount of actuation of an actuation control 120 of a plurality of actuation controls 120. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

Figure 7A:
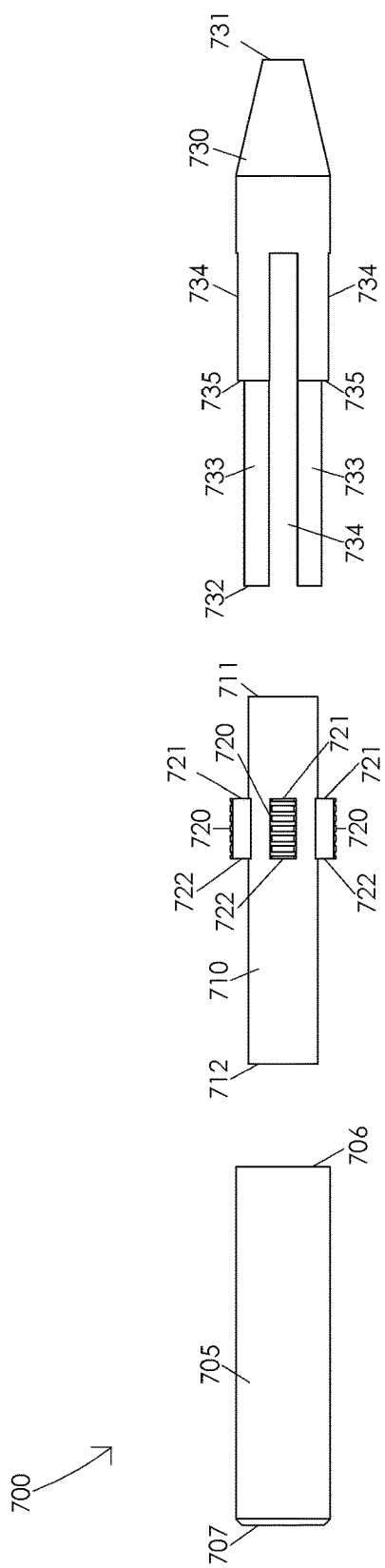
FIGS. 7A and 7B are schematic diagrams illustrating an exploded view of a handle assembly.
Figure 7B:
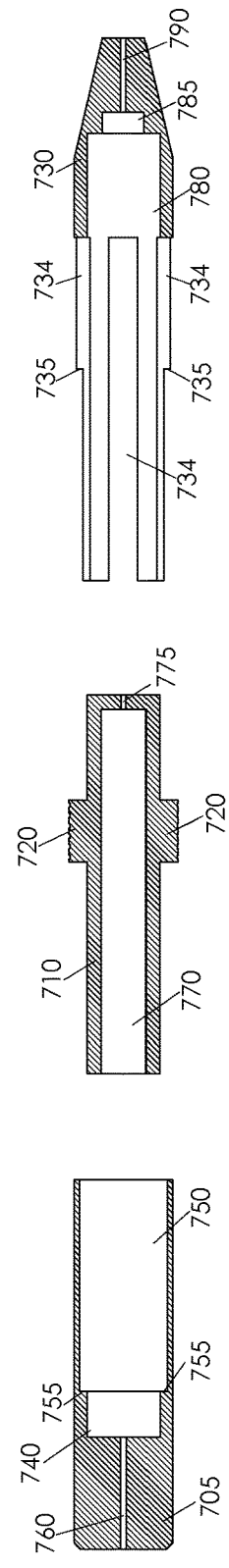

FIGS. 7A and 7B are schematic diagrams illustrating an exploded view of a handle assembly 700. FIG. 7A illustrates a side view of handle assembly 700. In one or more embodiments, handle assembly 700 may comprise a handle end cap 705 having a handle end cap distal end 706 and a handle end cap proximal end 707, an actuation mechanism 710 having an actuation mechanism distal end 711 and an actuation mechanism proximal end 712, and a handle base 730 having a handle base distal end 731 and a handle base proximal end 732. Illustratively, actuation mechanism 710 may comprise a plurality of actuation controls 720. For example, each actuation control 720 of a plurality of actuation controls 720 may comprise an actuation control distal end 721 and an actuation control proximal end 722. In one or more embodiments, handle base 730 may comprise a plurality of handle base limbs 733, a plurality of handle base channels 734, and a handle end cap interface 735.

FIG. 7B illustrates a cross-sectional view of handle assembly 700. In one or more embodiments, handle assembly 700 may comprise a proximal chamber 740, a handle base housing 750, a handle base interface 755, a cable housing 760, an inner bore 770, a flexible housing tube housing 775, an actuation mechanism guide 780, a pressure mechanism housing 785, and a flexible housing tube guide 790. Handle end cap 705, actuation mechanism 710, actuation control 720, and handle base 730 may be manufactured from any suitable material, e.g., polymers, metals, metal alloys, etc., or from any combination of suitable materials.

Figure 8A:
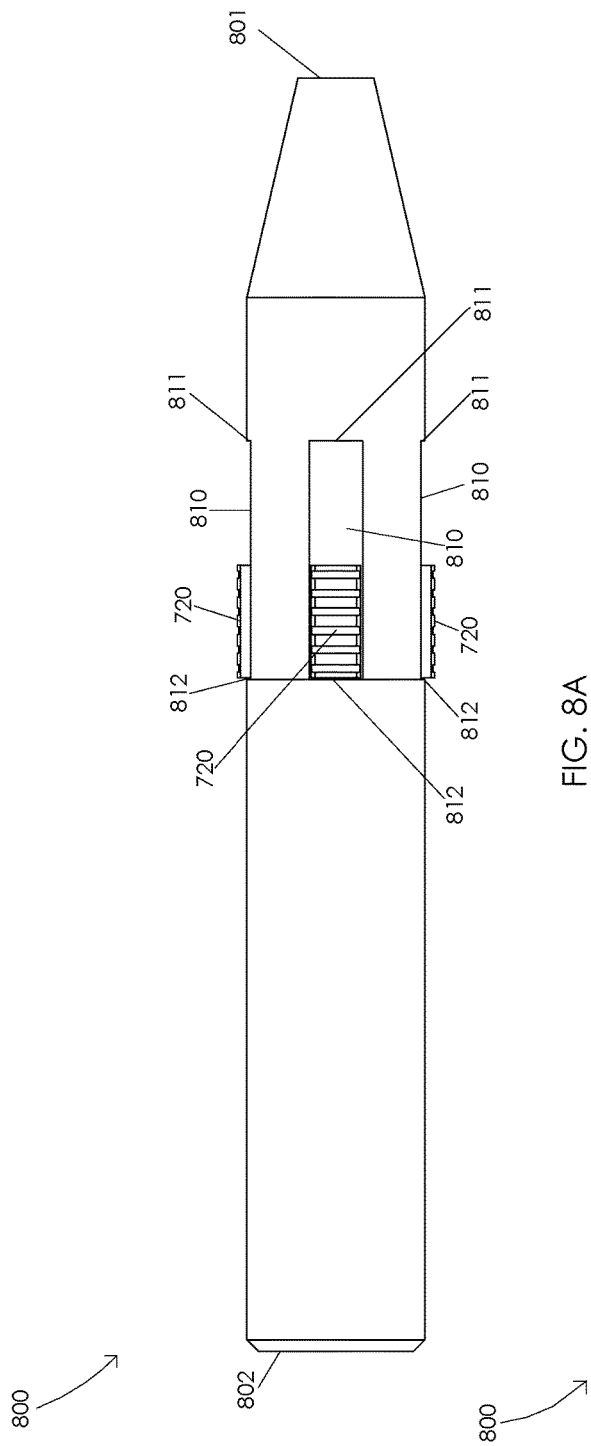
FIGS. 8A and 8B are schematic diagrams illustrating a handle.
Figure 8B:
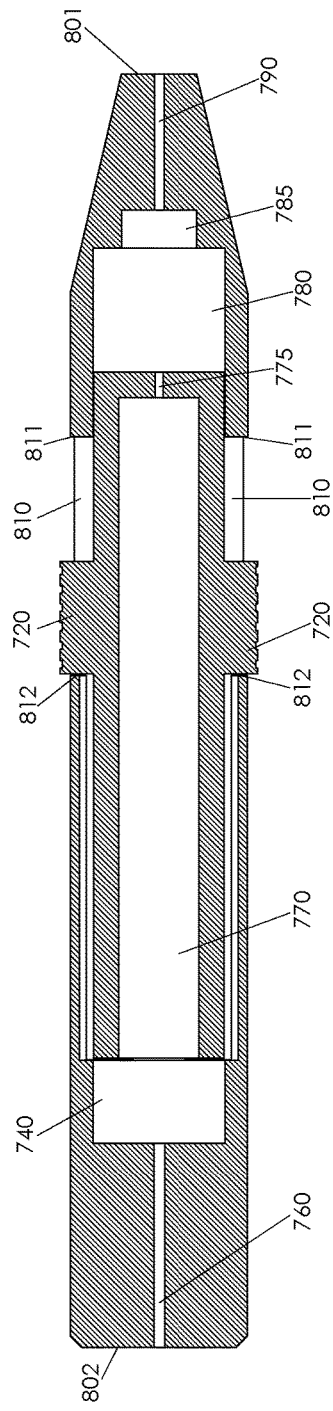

FIGS. 8A and 8B are schematic diagrams illustrating a handle 800. FIG. 8A illustrates a side view of handle 800. In one or more embodiments, handle 800 may comprise a handle distal end 801, a handle proximal end 802, and a plurality of actuation control guides 810. For example, each actuation control guide 810 of a plurality of actuation control guides 810 may comprise an actuation control guide distal end 811 and an actuation control guide proximal end 812. Illustratively, handle distal end 801 may comprise handle base distal end 731. In one or more embodiments, handle proximal end 802 may comprise handle end cap proximal end 707.

FIG. 8B illustrates a cross-sectional view of handle 800. Illustratively, actuation mechanism 710 may be disposed within handle end cap 705 and handle base 730. In one or more embodiments, a portion of actuation mechanism 710 may be disposed within handle base housing 750, e.g., actuation mechanism proximal end 712 may be disposed within handle base housing 750. Illustratively, a portion of actuation mechanism 710 may be disposed within actuation mechanism guide 780, e.g., actuation mechanism distal end 711 may be disposed within actuation mechanism guide 780. In one or more embodiments, a portion of handle base 730 may be disposed within handle end cap 705, e.g., handle base proximal end 732 may be disposed within handle end cap 705. Illustratively, a portion of handle base 730 may be disposed within handle base housing 750. In one or more embodiments, a portion of handle base 730 may be disposed within handle base housing 750, e.g., handle base proximal end 732 may be configured to interface with handle base interface 755. Illustratively, a portion of handle base 730 may be disposed within handle base housing 750, e.g., handle end cap distal end 706 may be configured to interface with handle end cap interface 735. In one or more embodiments, a portion of handle base 730 may be fixed within a portion of handle end cap 705, e.g., by an adhesive or any suitable fixation means. For example, a portion of handle base 730 may be fixed within handle base housing 750, e.g., by an adhesive or any suitable fixation means.

Illustratively, each actuation control 720 of a plurality of actuation controls 720 may be disposed within an actuation control guide 810 of a plurality of actuation control guides 810. In one or more embodiments, each actuation control guide 810 of a plurality of actuation control guides 810 may comprise a handle base channel 734 of a plurality of handle base channels 734. In one or more embodiments, at least one actuation control 720 may be configured to actuate within at least one actuation control guide 810. Illustratively, each actuation control 720 of a plurality of actuation controls 720 may be configured to actuate within an actuation control guide 810 of a plurality of actuation control guides 810. In one or more embodiments, an actuation of a particular actuation control 720 in a particular actuation control guide 810 may be configured to actuate each actuation control 720 of a plurality of actuation controls 720. In one or more embodiments, actuation controls 720 may be configured to actuate within actuation control guides 810 in pairs or groups. Illustratively, an actuation of first actuation control 720 within a first actuation control guide 810 may be configured to actuate a second actuation control 720 within a second actuation control guide 810.

In one or more embodiments, actuation mechanism 710 may be configured to actuate within actuation mechanism guide 780. For example, actuation mechanism guide 780 may comprise a lubricant configured to facilitate an actuation of actuation mechanism 710 within actuation mechanism guide 780. Illustratively, an actuation of an actuation control 720 within an actuation control guide 810 may be configured to actuate actuation mechanism 710, e.g., within actuation mechanism guide 780. In one or more embodiments, an actuation of an actuation control 720 towards an actuation control guide distal end 811, e.g., and away from an actuation control guide proximal end 812, may be configured to actuate actuation mechanism 710 towards handle distal end 801, e.g., and away from handle proximal end 802. Illustratively, an actuation of an actuation control 720 towards an actuation control guide proximal end 812, e.g., and away from an actuation control guide distal end 811, may be configured to actuate actuation mechanism towards handle proximal end 802, e.g., and away from handle distal end 801.

In one or more embodiments, a surgeon may actuate actuation mechanism 710 within actuation mechanism guide 780, e.g., by manipulating an actuation control 720 of a plurality of actuation controls 720 when handle 800 is in a first rotational orientation. Illustratively, the surgeon may rotate handle 800 and actuate actuation mechanism 710 within actuation mechanism guide 780, e.g., by manipulating an actuation control 720 of a plurality of actuation controls 720 when handle 800 is in a second rotational orientation. In one or more embodiments, the surgeon may rotate handle 800 and actuate actuation mechanism 710 within actuation mechanism guide 780, e.g., by manipulating an actuation control 720 of a plurality of actuation controls 720 when handle 800 is in a third rotational orientation. Illustratively, a surgeon may actuate actuation mechanism 710 within actuation mechanism guide 780, e.g., by manipulating an actuation control 720 of a plurality of actuation controls 720 when handle 800 is in any rotational orientation of a plurality of rotational orientations.

Figure 9:
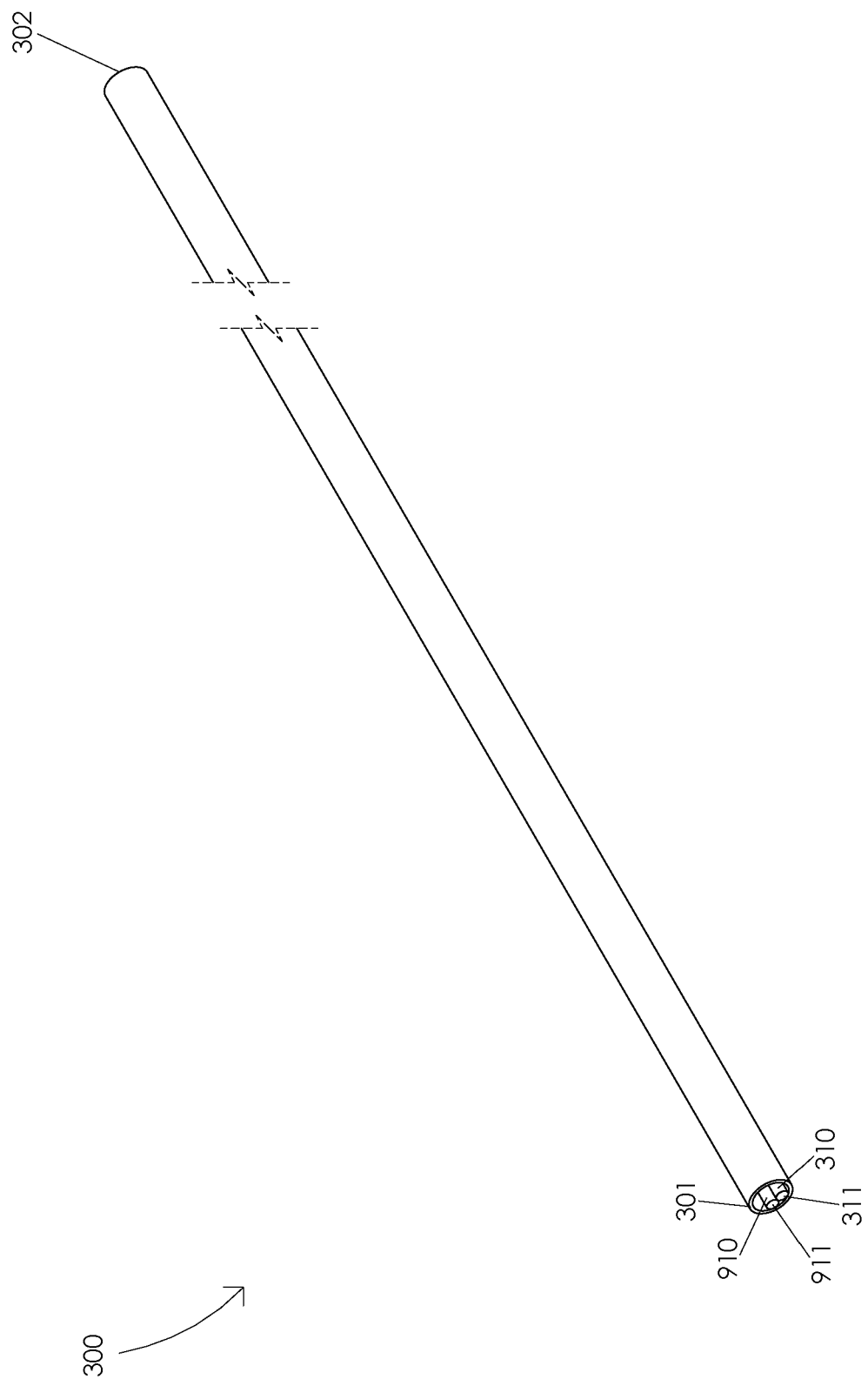
FIG. 9 is a schematic diagram illustrating a flexible housing tube.

FIG. 9 is a schematic diagram illustrating a flexible housing tube 300. Illustratively, flexible housing tube 300 may comprise a flexible housing tube distal end 301 and a flexible housing tube proximal end 302. Flexible housing tube 300 may be manufactured from any suitable material, e.g., polymers, metals, metal alloys, etc., or from any combination of suitable materials. Illustratively, flexible housing tube 300 may comprise a shape memory material, e.g., Nitinol. In one or more embodiments, flexible housing tube 300 may be manufactured from a material having an ultimate tensile strength between 700 and 1000 MPa. Illustratively, flexible housing tube 300 may be manufactured from a material having ultimate tensile strength less than 700 MPa or greater than 1000 MPa. In one or more embodiments, flexible housing tube 300 may be manufactured from a material having a modulus of elasticity between 30 and 80 GPa. Illustratively, flexible housing tube 300 may be manufactured from a material having a modulus of elasticity less than 30 GPa or greater than 80 GPa.

In one or more embodiments, flexible housing tube 300 may be manufactured with dimensions suitable for performing microsurgical procedures, e.g., ophthalmic surgical procedures. Illustratively, flexible housing tube 300 may be manufactured at gauge sizes commonly used in ophthalmic surgical procedures, e.g., 23 gauge, 25 gauge, etc. In one or more embodiments, flexible housing tube 300 may be configured to be inserted in a cannula, e.g., a cannula used during an ophthalmic surgical procedure. For example, one or more properties of flexible housing tube 300 may be optimized to reduce friction as flexible housing tube 300 is inserted into a cannula. In one or more embodiments, one or more properties of flexible housing tube 300 may be optimized to reduce friction as flexible housing tube 300 is removed from a cannula. Illustratively, flexible housing tube 300 may have an ultimate tensile strength between 1000 MPa and 1100 MPa. In one or more embodiments, flexible housing tube 300 may have an ultimate tensile strength less than 1000 MPa or greater than 1100 MPa.

In one or more embodiments, an optic fiber 310 may be disposed within flexible housing tube 300. Illustratively, optic fiber 310 may comprise an optic fiber distal end 311 and an optic fiber proximal end 312. In one or more embodiments, optic fiber 310 may be configured to transmit light, e.g., laser light. Illustratively, optic fiber 310 may be disposed within flexible housing tube 300 wherein optic fiber distal end 311 may be adjacent to flexible housing tube distal end 301. In one or more embodiments, a portion of optic fiber 310 may be fixed to a portion of flexible housing tube 300, e.g., by an adhesive or any suitable fixation means.

In one or more embodiments, a cable 910 may be disposed within flexible housing tube 300. Illustratively, cable 910 may comprise a cable distal end 911 and a cable proximal end 912. In one or more embodiments, cable 910 may be disposed within flexible housing tube 300 wherein cable distal end 911 may be adjacent to flexible housing tube distal end 301. Illustratively, a portion of cable 910 may be fixed to a portion of flexible housing tube 300, e.g., by an adhesive or any suitable fixation means.

Figure 10:
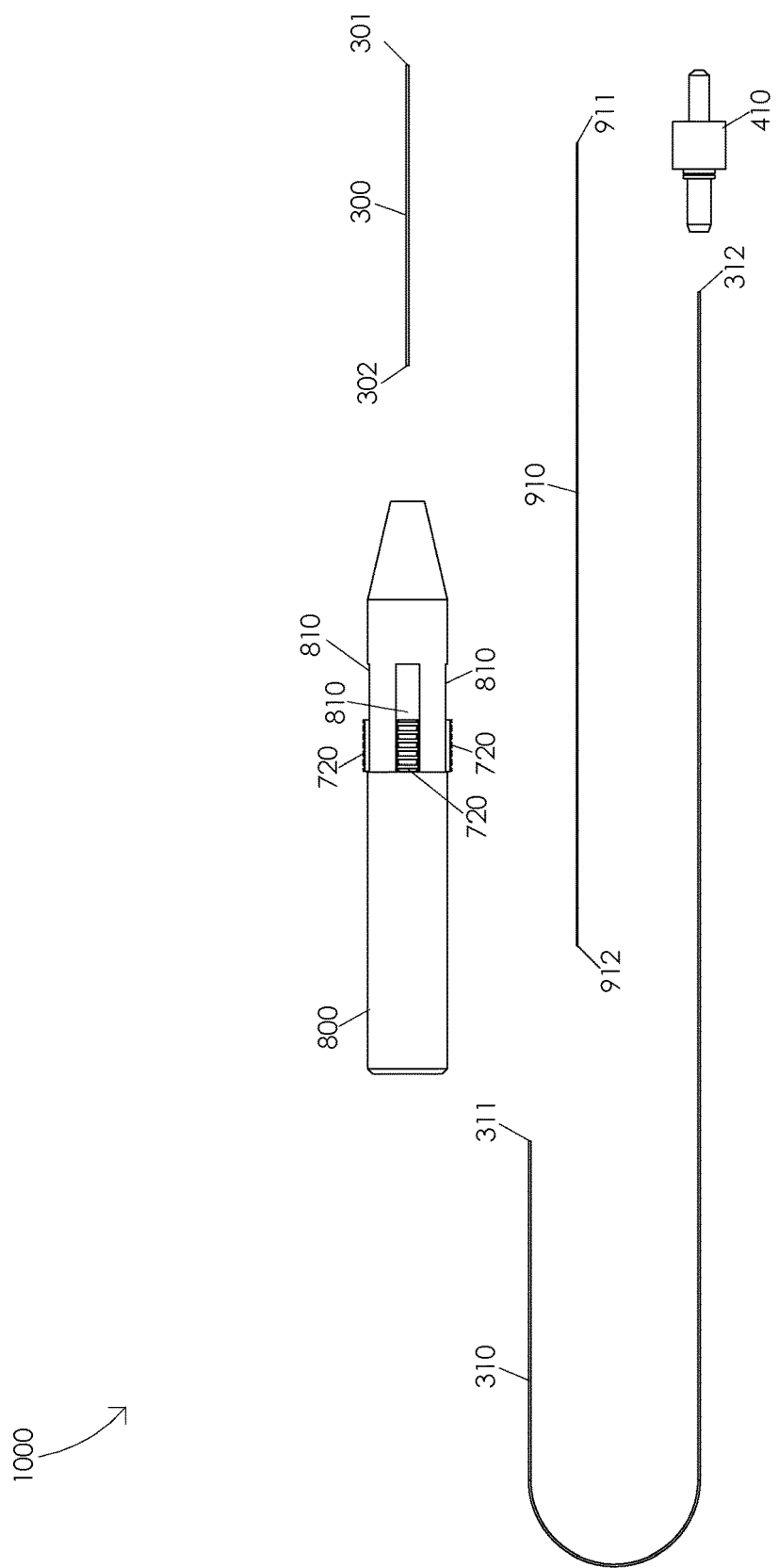
FIG. 10 is a schematic diagram illustrating an exploded view of a steerable laser probe assembly.

FIG. 10 is a schematic diagram illustrating an exploded view of a steerable laser probe assembly 1000. In one or more embodiments, steerable laser probe assembly 1000 may comprise a handle 800, a flexible housing tube 300 having a flexible housing tube distal end 301 and a flexible housing tube proximal end 302, an optic fiber 310 having an optic fiber distal end 311 and an optic fiber proximal end 312, a cable 910 having a cable distal end 911 and a cable proximal end 912, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of flexible housing tube 300 may be fixed to actuation mechanism 710, e.g., flexible housing tube proximal end 302 may be fixed to actuation mechanism distal end 711. In one or more embodiments, a portion of flexible housing tube 300 may be fixed to actuation mechanism 710, e.g., by an adhesive or any suitable fixation means. Illustratively, a portion of flexible housing tube 300 may be disposed within actuation mechanism 710, e.g., flexible housing tube proximal end 302 may be disposed within flexible housing tube housing 775. In one or more embodiments, a portion of flexible housing tube 300 may be fixed within flexible housing tube housing 775, e.g., by an adhesive or any suitable fixation means. Illustratively, flexible housing tube 300 may be disposed within actuation mechanism guide 780 and flexible housing tube guide 790. In one or more embodiments, a portion of flexible housing tube 300 may extend from handle distal end 801, e.g., flexible housing tube distal end 301 may extend from handle distal end 801.

Illustratively, optic fiber 310 may be disposed within cable housing 760, proximal chamber 740, inner bore 770, flexible housing tube housing 775, flexible housing tube 300, actuation mechanism guide 780, and flexible housing tube guide 990. In one or more embodiments, a portion of optic fiber 310 may be fixed to a portion of flexible housing tube 300, e.g., by an adhesive or any suitable fixation means. Illustratively, cable 910 may be disposed within cable housing 760, proximal chamber 740, inner bore 770, flexible housing tube housing 775, flexible housing tube 300, actuation mechanism guide 780, and flexible housing tube guide 990. In one or more embodiments, a portion of cable 910 may be fixed to a portion of flexible housing tube 300, e.g., by an adhesive or any suitable fixation means. Illustratively, a portion of cable 910 may be fixed in a position relative to handle 800. In one or more embodiments, a portion of cable 910 may be fixed within cable housing 760, e.g., by an adhesive or any suitable fixation means. Illustratively, a portion of cable 910 may be fixed within cable housing 760, e.g., by a press fit or any suitable fixation means. In one or more embodiments, a portion of cable 910 may be fixed to a portion of flexible housing tube 300 and a portion of cable 910 may be fixed in a position relative to handle 800.

Illustratively, an actuation of an actuation control 720 within an actuation control guide 810, e.g., towards actuation control guide distal end 811 and away from actuation control guide proximal end 812, may be configured to actuate actuation mechanism 710 within actuation mechanism guide 780, e.g., towards handle distal end 801 and away from handle proximal end 802. In one or more embodiments, an actuation of actuation mechanism 710 towards handle distal end 801 and away from handle proximal end 802 may be configured to extend actuation mechanism 710 relative to cable 910. Illustratively, an extension of actuation mechanism 710 relative to cable 910 may be configured to extend flexible housing tube 300 relative to cable 910. In one or more embodiments, cable 910 may be configured to resist an extension of flexible housing tube 300 relative to cable 910. Illustratively, cable 910 may be configured to resist an extension of flexible housing tube 300 relative to cable 910, e.g., a portion of cable 910 may be configured to apply a force to a portion of flexible housing tube 300. In one or more embodiments, an application of a force, e.g., a resistive force, to a portion of flexible housing tube 300 may be configured to compress a portion of flexible housing tube 300 causing flexible housing tube 300 to gradually curve. Illustratively, a gradual curving of flexible housing tube 300 may be configured to gradually curve optic fiber 310. In one or more embodiments, an actuation of an actuation control 720 within an actuation control guide 810, e.g., towards actuation control guide distal end 811 and away from actuation control guide proximal end 812, may be configured to gradually curve optic fiber 310.

Illustratively, an actuation of an actuation control 720 within an actuation control guide 810, e.g., towards actuation control guide proximal end 812 and away from actuation control guide distal end 811, may be configured to actuate actuation mechanism 710 within actuation mechanism guide 780, e.g., towards handle proximal end 802 and away from handle distal end 801. In one or more embodiments, an actuation of actuation mechanism 710 towards handle proximal end 802 and away from handle distal end 801 may be configured to retract actuation mechanism 710 relative to cable 910. Illustrative a retraction of actuation mechanism 710 relative to cable 910 may be configured to retract flexible housing tube 300 relative to cable 910. In one or more embodiments, cable 910 may be configured to facilitate a retraction of flexible housing tube 300 relative to cable 910. Illustratively, cable 910 may be configured to facilitate a retraction of flexible housing tube 300 relative to cable 910, e.g., a portion of cable 910 may be configured to reduce a force applied to a portion of flexible housing tube 300. In one or more embodiments, a reduction of a force, e.g., a resistive force, applied to a portion of flexible housing tube 300 may be configured to decompress a portion of flexible housing tube 300 causing flexible housing tube 300 to gradually straighten. Illustratively, a gradual straightening of flexible housing tube 300 may be configured to gradually straighten optic fiber 310. In one or more embodiments, an actuation of an actuation control 720 within an actuation control guide 810, e.g., towards actuation control guide proximal end 812 and away from actuation control guide distal end 811, may be configured to gradually straighten optic fiber 310.

Figure 11A:
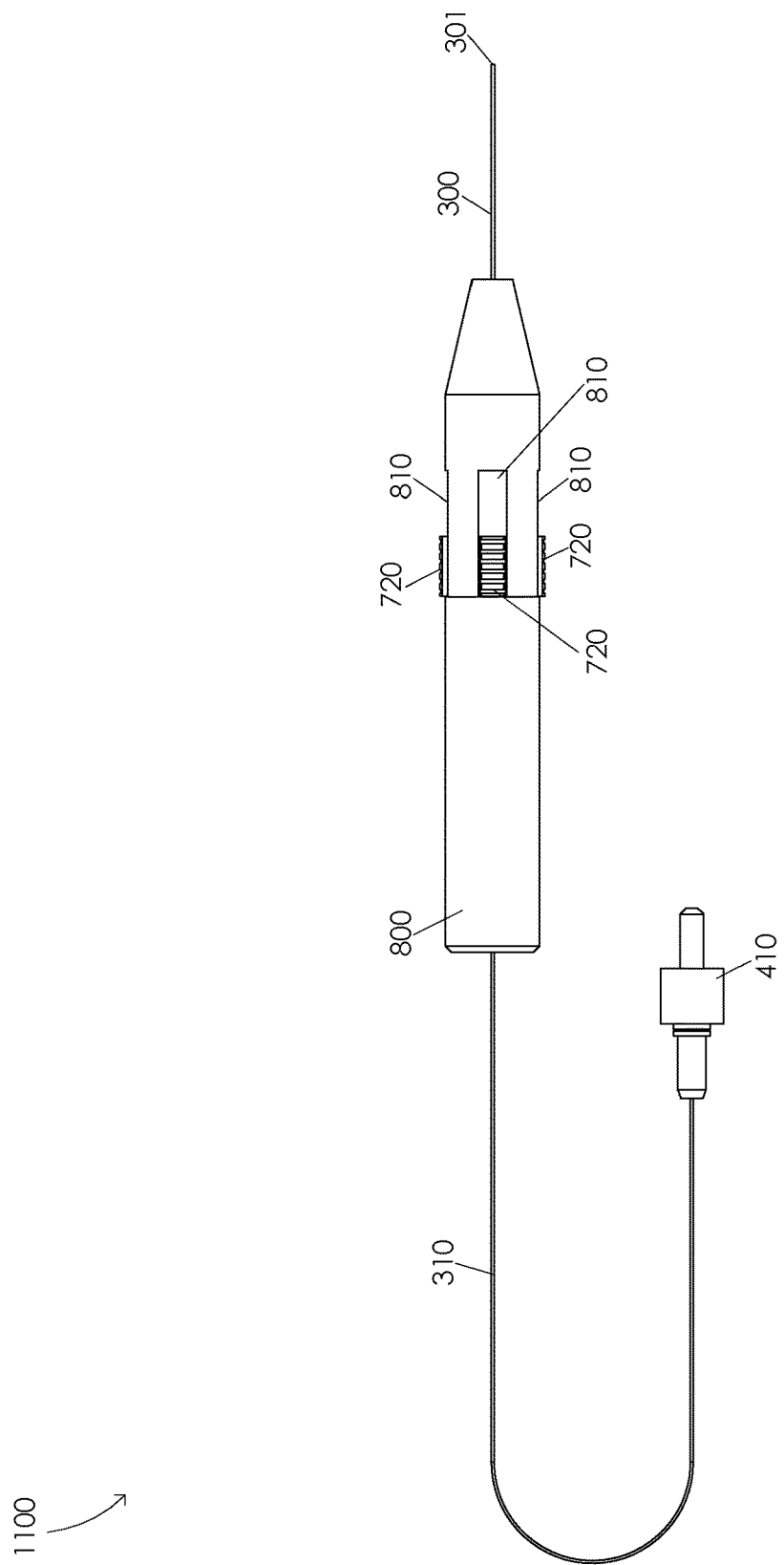
FIGS. 11A, 11B, 11C, 11D, and 11E are schematic diagrams illustrating a gradual curving of an optic fiber.

FIGS. 11A, 11B, 11C, 11D, and 11E are schematic diagrams illustrating a gradual curving of an optic fiber 310. FIG. 11A illustrates a straight optic fiber 1100. In one or more embodiments, optic fiber 310 may comprise a straight optic fiber 1100, e.g., when flexible housing tube 300 is fully retracted relative to handle proximal end 802. Illustratively, optic fiber 310 may comprise a straight optic fiber 1100, e.g., when an actuation control 720 of a plurality of actuation controls 720 is fully retracted relative to an actuation control guide proximal end 812. In one or more embodiments, optic fiber 310 may comprise a straight optic fiber 1100, e.g., when actuation mechanism 710 is fully retracted relative to handle proximal end 802. Illustratively, a line tangent to optic fiber distal end 311 may be parallel to a line tangent to flexible housing tube proximal end 302, e.g., when optic fiber 310 comprises a straight optic fiber 1100.

Figure 11B:
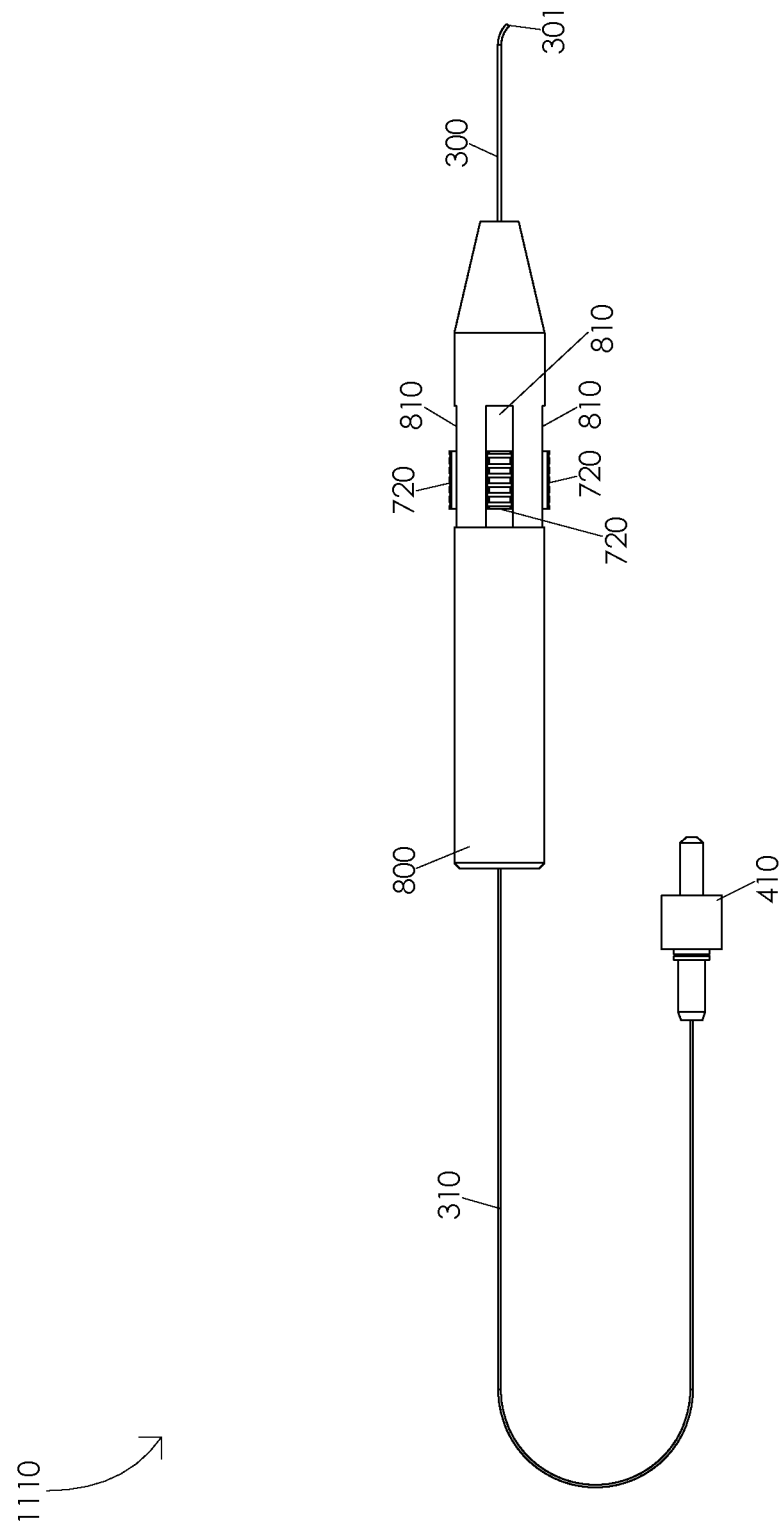

FIG. 11B illustrates an optic fiber in a first curved position 1110. In one or more embodiments, an actuation of an actuation control 720 within an actuation control guide 810, e.g., towards actuation control guide distal end 811 and away from actuation control guide proximal end 812, may be configured to gradually curve optic fiber 310 from a straight optic fiber 1100 to an optic fiber in a first curved position 1110. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend flexible housing tube 300 relative to cable 910. Illustratively, a portion of cable 910, e.g., a portion of cable 910 fixed to a portion of flexible housing tube 300, may be configured to resist an extension of flexible housing tube 300 relative to cable 910. In one or more embodiments, an extension of flexible housing tube 300 relative to cable 910 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from a straight optic fiber 1100 to an optic fiber in a first curved position 1110. In one or more embodiments, a line tangent to optic fiber distal end 311 may intersect a line tangent to flexible housing tube proximal end 302 at a first angle, e.g., when optic fiber 310 comprises an optic fiber in a first curved position 1110. Illustratively, the first angle may comprise any angle greater than zero degrees. For example, the first angle may comprise a 45 degree angle.

Figure 11C:
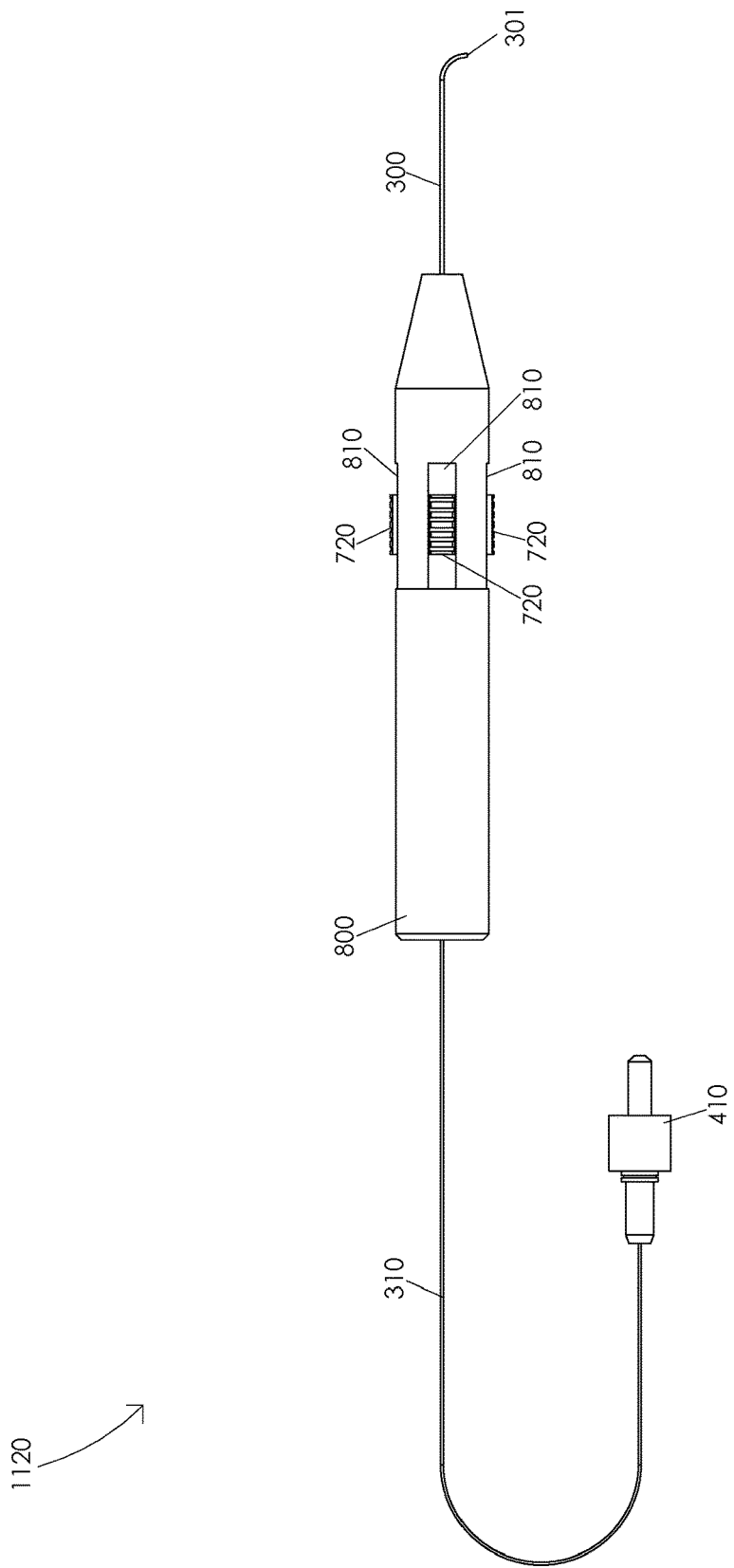

FIG. 11C illustrates an optic fiber in a second curved position 1120. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a first curved position 1110 to an optic fiber in a second curved position 1120. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend flexible housing tube 300 relative to cable 910. Illustratively, a portion of cable 910, e.g., a portion of cable 910 fixed to a portion of flexible housing tube 300, may be configured to resist an extension of flexible housing tube 300 relative to cable 910. In one or more embodiments, an extension of flexible housing tube 300 relative to cable 910 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a first curved position 1110 to an optic fiber in a second curved position 1120. In one or more embodiments, a line tangent to optic fiber distal end 311 may intersect a line tangent to flexible housing tube proximal end 302 at a second angle, e.g., when optic fiber 310 comprises an optic fiber in a second curved position 1120. Illustratively, the second angle may comprise any angle greater than the first angle. For example, the second angle may comprise a 90 degree angle.

Figure 11D:
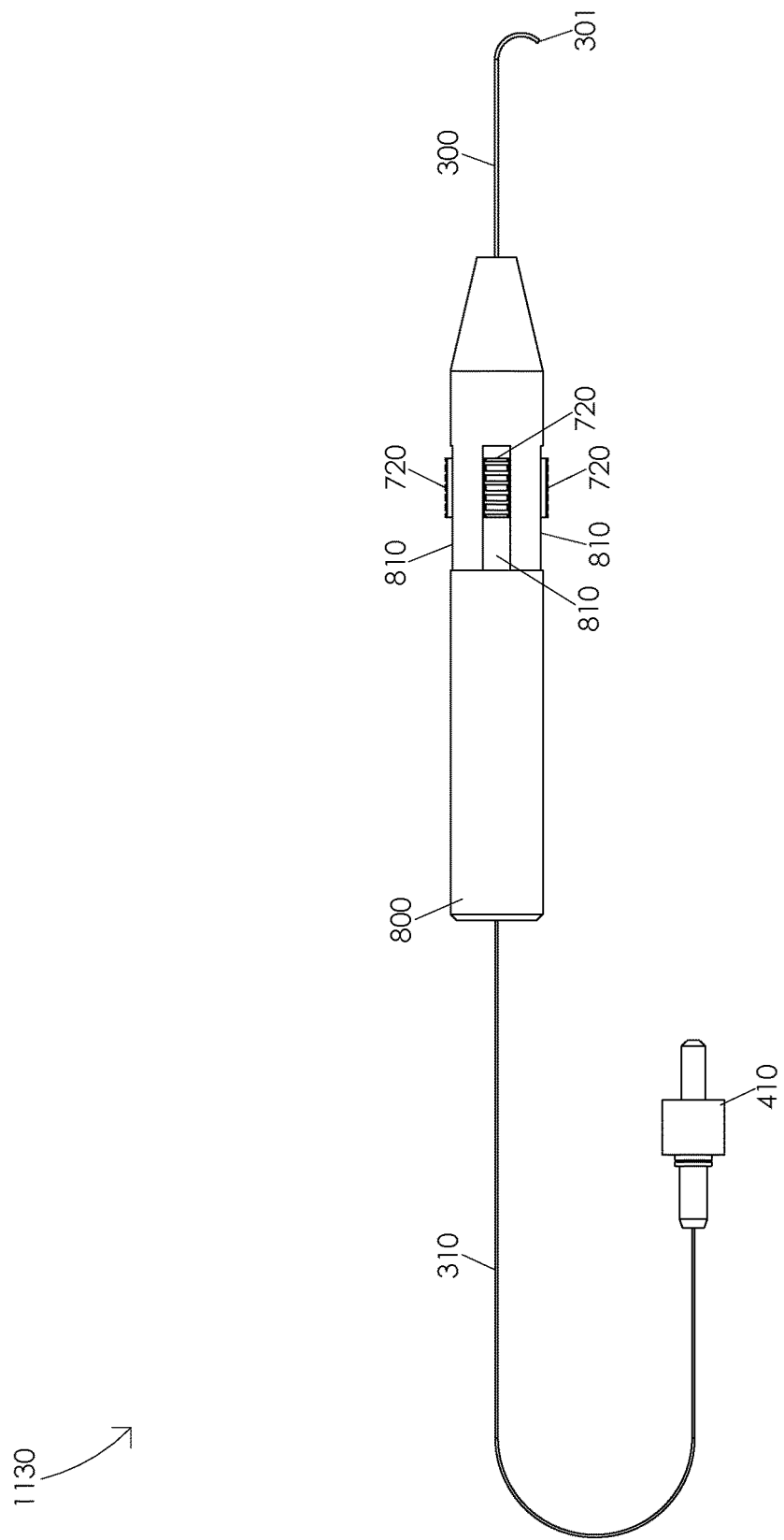

FIG. 11D illustrates an optic fiber in a third curved position 1130. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a second curved position 1120 to an optic fiber in a third curved position 1130. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend flexible housing tube 300 relative to cable 910. Illustratively, a portion of cable 910, e.g., a portion of cable 910 fixed to a portion of flexible housing tube 300, may be configured to resist an extension of flexible housing tube 300 relative to cable 910. In one or more embodiments, an extension of flexible housing tube 300 relative to cable 910 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a second curved position 1120 to an optic fiber in a third curved position 1130. In one or more embodiments, a line tangent to optic fiber distal end 311 may intersect a line tangent to flexible housing tube proximal end 302 at a third angle, e.g., when optic fiber 310 comprises an optic fiber in a third curved position 1130. Illustratively, the third angle may comprise any angle greater than the second angle. For example, the third angle may comprise a 135 degree angle.

Figure 11E:
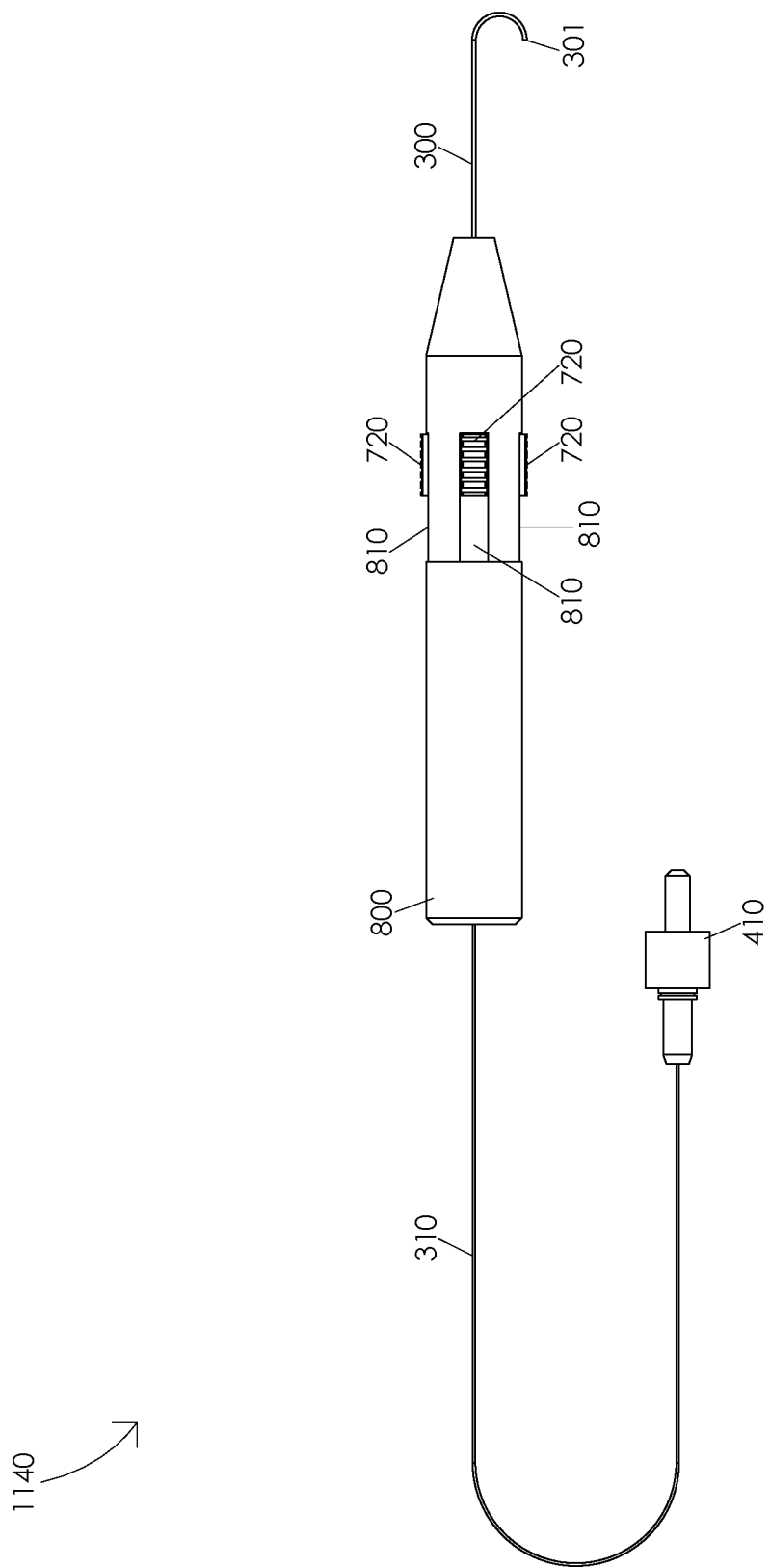

FIG. 11E illustrates an optic fiber in a fourth curved position 1140. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a third curved position 1130 to an optic fiber in a fourth curved position 1140. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend flexible housing tube 300 relative to cable 910. Illustratively, a portion of cable 910, e.g., a portion of cable 910 fixed to a portion of flexible housing tube 300, may be configured to resist an extension of flexible housing tube 300 relative to cable 910. In one or more embodiments, an extension of flexible housing tube 300 relative to cable 910 may be configured to apply a force to a portion of flexible housing tube 300. Illustratively, an application of a force to a portion of flexible housing tube 300 may be configured to cause flexible housing tube 300 to gradually curve, e.g., by compressing a portion of flexible housing tube 300. In one or more embodiments, a gradual curving of flexible housing tube 300 may be configured to gradually curve optic fiber 310, e.g., from an optic fiber in a third curved position 1130 to an optic fiber in a fourth curved position 1140. In one or more embodiments, a line tangent to optic fiber distal end 311 may be parallel to a line tangent to flexible housing tube proximal end 302, e.g., when optic fiber 310 comprises an optic fiber in a fourth curved position 1140.

In one or more embodiments, one or more properties of a steerable laser probe may be adjusted to attain one or more desired steerable laser probe features. Illustratively, a length that flexible housing tube distal end 301 extends from actuation mechanism distal end 711 may be adjusted to vary an amount of actuation of an actuation control 720 of a plurality of actuation controls 720 configured to curve flexible housing tube 300 to a particular curved position. In one or more embodiments, a stiffness of flexible housing tube 300 may be adjusted to vary an amount of actuation of an actuation control 720 of a plurality of actuation controls 720 configured to curve flexible housing tube 300 to a particular curved position. Illustratively, flexible housing tube 300 may comprise a solid tube structure. In one or more embodiments, flexible housing tube 300 may comprise one or more apertures, e.g., configured to vary a stiffness of flexible housing tube 300. Illustratively, a material comprising flexible housing tube 300 may be adjusted to vary an amount of actuation of an actuation control 720 of a plurality of actuation controls 720 configured to curve flexible housing tube 300 to a particular curved position. In one or more embodiments, a stiffness of flexible housing tube 300 may be adjusted to vary a bend radius of flexible housing tube 300. Illustratively, a stiffness of flexible housing tube 300 may be adjusted to vary a radius of curvature of flexible housing tube 300, e.g., when flexible housing tube 300 is in a particular curved position.

In one or more embodiments, a geometry of actuation mechanism 710 may be adjusted to vary an amount of actuation of an actuation control 720 of a plurality of actuation controls 720 configured to curve flexible housing tube 300 to a particular curved position. Illustratively, a geometry of actuation mechanism guide 780 may be adjusted to vary an amount of actuation of an actuation control 720 of a plurality of actuation controls 720 configured to curve flexible housing tube 300 to a particular curved position. In one or more embodiments, a geometry of handle end cap 705 or a geometry of handle base 730 may be adjusted to vary an amount of actuation of an actuation control 720 of a plurality of actuation controls 720 configured to curve flexible housing tube 300 to a particular curved position. Illustratively, one or more locations within flexible housing tube 300 wherein optic fiber 310 may be fixed to a portion of flexible housing tube 300 may be adjusted to vary an amount of actuation of an actuation control 720 of a plurality of actuation controls 720 configured to curve flexible housing tube 300 to a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to an actuation of an actuation control 720 of a plurality of actuation controls 720. In one or more embodiments, a portion of a steerable laser probe, e.g., handle 800, may be marked in a manner configured to indicate a direction that optic fiber 310 may curve. For example, a portion of flexible housing tube 300 may comprise a mark configured to indicate a direction that optic fiber 310 may curve. Illustratively, flexible housing tube 300 may comprise a slight curve, e.g., a curve less than 7.5 degrees, when an actuation control 720 of a plurality of actuation controls 720 is fully retracted relative to an actuation control guide proximal end 812. In one or more embodiments, flexible housing tube 300 may comprise a slight curve configured to indicate a direction that optic fiber 310 may curve, e.g., due to an extension of an actuation control 720 of a plurality of actuation controls 720 relative to an actuation control guide proximal end 812.

In one or more embodiments, a steerable laser probe may comprise a pressure mechanism configured to provide a force. Illustratively, a pressure mechanism may be disposed within pressure mechanism housing 785. For example, a pressure mechanism may be disposed within proximal chamber 740. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 710 relative to handle proximal end 802. Illustratively, a pressure mechanism may be configured to provide a facilitating force, e.g., to facilitate a retraction of actuation mechanism 710 relative to handle proximal end 802. In one or more embodiments, a pressure mechanism may be configured to provide a resistive force, e.g., to resist a retraction of actuation mechanism 710 relative to handle proximal end 802. Illustratively, a pressure mechanism may be configured to provide a facilitating force, e.g., to facilitate an extension of actuation mechanism 710 relative to handle proximal end 802. In one or more embodiments, a pressure mechanism may comprise a spring or a coil. Illustratively, a pressure mechanism may comprise a pneumatic system or any system configured to provide a force.

In one or more embodiments, one or more actuation controls 720 may be fixed together. For example, a first actuation control 720 may be connected to a second actuation control 720 wherein an actuation of the first actuation control 720 is configured to actuate the second actuation control 720 and an actuation of the second actuation control 720 is configured to actuate the first actuation control 720. Illustratively, each actuation control 720 of a plurality of actuation controls 720 may be connected wherein an actuation of a particular actuation control 720 is configured to actuate each actuation control 720 of the plurality of actuation controls 720. In one or more embodiments, each actuation control 720 may be connected to another actuation control 720 of a plurality of actuation controls 720, e.g., by a ring or any suitable structure wherein a surgeon may actuate each actuation control 720 of the plurality of actuation controls 720 in any rotational orientation of handle 800.

Illustratively, cable 910 may be fixed to flexible housing tube 300 at a plurality of fixation points, e.g., to vary one or more properties of a steerable laser probe. In one or more embodiments, a length of cable 910 may be adjusted to vary an amount of extension of an actuation control 720 of a plurality of actuation controls 720 relative to handle proximal end 802 configured to curve flexible housing tube 300 to a particular curved position. Illustratively, a steerable laser probe may comprise one or more redundant cables 910. In one or more embodiments, one or more redundant cables 910 may be configured to maintain a particular curved position of flexible housing tube 300, e.g., in the event that cable 910 breaks or fails. Illustratively, one or more redundant cables 910 may be configured to maintain a particular curved position of flexible housing tube 300, e.g., in the event that a cable 910 fixation means fails. In one or more embodiments, one or more redundant cables 910 may be configured to maintain a particular curved position of flexible housing tube 300, e.g., in the event that cable 910 is no longer configured to maintain the particular curved position of flexible housing tube 300. Illustratively, one or more redundant cables 910 may be configured to maintain a particular curved position of flexible housing tube 300 wherein cable 910 is also configured to maintain the particular curved position of flexible housing tube 300.

In one or more embodiments, flexible housing tube 300 may comprise an access window configured to allow access to a portion cable 910. Illustratively, cable 910 may be fixed to a portion of flexible housing tube 300, e.g., by looping a portion of cable 910 through an aperture in flexible housing tube 300. In one or more embodiments, cable 910 may be fixed to a portion of flexible housing tube 300, e.g., by a purely mechanical means. For example, cable 910 may be fixed to a portion of flexible housing tube 300 in a manner other than by an adhesive, a weld, etc. Illustratively, cable 910 may be fixed to a portion of flexible housing tube 300 wherein a portion of cable 910 is configured to fail at a first applied failure force and a fixation means that fixes a portion of cable 910 to a portion of flexible housing tube 300 is configured to fail at a second applied failure force. In one or more embodiments, the second applied failure force may be greater than the first applied failure force.

Figure 12A:
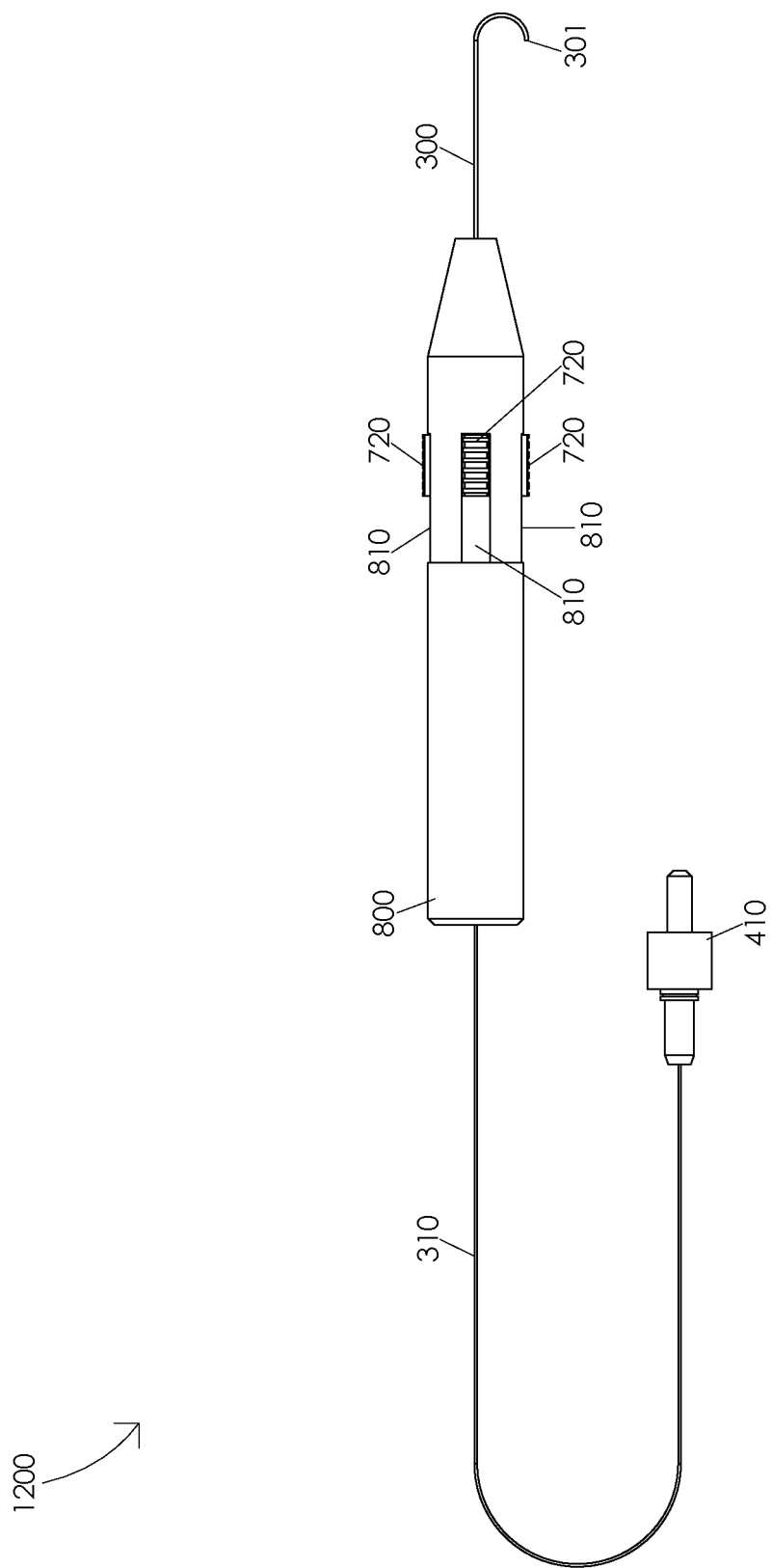
FIGS. 12A, 12B, 12C, 12D, and 12E are schematic diagrams illustrating a gradual straightening of an optic fiber.

FIGS. 12A, 12B, 12C, 12D, and 12E are schematic diagrams illustrating a gradual straightening of an optic fiber 310. FIG. 12A illustrates a fully curved optic fiber 1200. In one or more embodiments, optic fiber 310 may comprise a fully curved optic fiber 1200, e.g., when flexible housing tube 300 is fully extended relative to handle proximal end 802. Illustratively, optic fiber 310 may comprise a fully curved optic fiber 1200, e.g., when an actuation control 720 of a plurality of actuation controls 720 is fully extended relative to an actuation control guide proximal end 812. In one or more embodiments, optic fiber 310 may comprise a fully curved optic fiber 1200, e.g., when actuation mechanism 710 is fully extended relative to handle proximal end 802. Illustratively, a line tangent to optic fiber distal end 311 may be parallel to a line tangent to flexible housing tube proximal end 302, e.g., when optic fiber 310 comprises a fully curved optic fiber 1200.

Figure 12B:
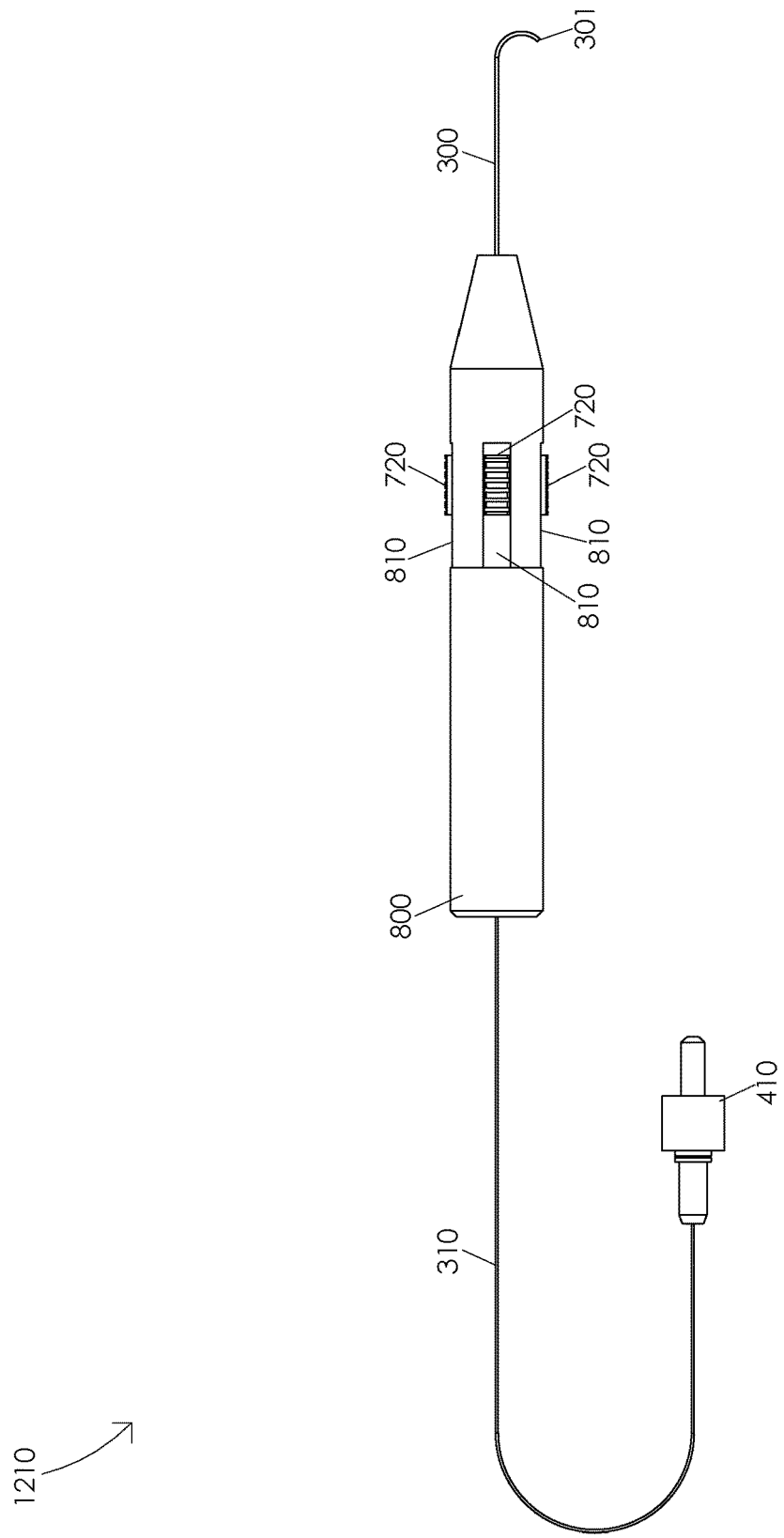

FIG. 12B illustrates an optic fiber in a first partially straightened position 1210. In one or more embodiments, an actuation of an actuation control 720 within an actuation control guide 810, e.g., towards actuation control guide proximal end 812 and away from actuation control guide distal end 811, may be configured to gradually straighten optic fiber 310 from a fully curved optic fiber 1200 to an optic fiber in a first partially straighten position 1210. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract flexible housing tube 300 relative to cable 910. Illustratively, a portion of cable 910, e.g., a portion of cable 910 fixed to a portion of flexible housing tube 300, may be configured to facilitate a retraction of flexible housing tube 300 relative to cable 910. In one or more embodiments, a retraction of flexible housing tube 300 relative to cable 910 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from a fully curved optic fiber 1200 to an optic fiber in a first partially straightened position 1210. In one or more embodiments, a line tangent to optic fiber distal end 311 may intersect a line tangent to flexible housing tube proximal end 302 at a first partially straightened angle, e.g., when optic fiber 310 comprises an optic fiber in a first partially straightened position 1210. Illustratively, the first partially straightened angle may comprise any angle less than 180 degrees. For example, the first partially straightened angle may comprise a 135 degree angle.

Figure 12C:
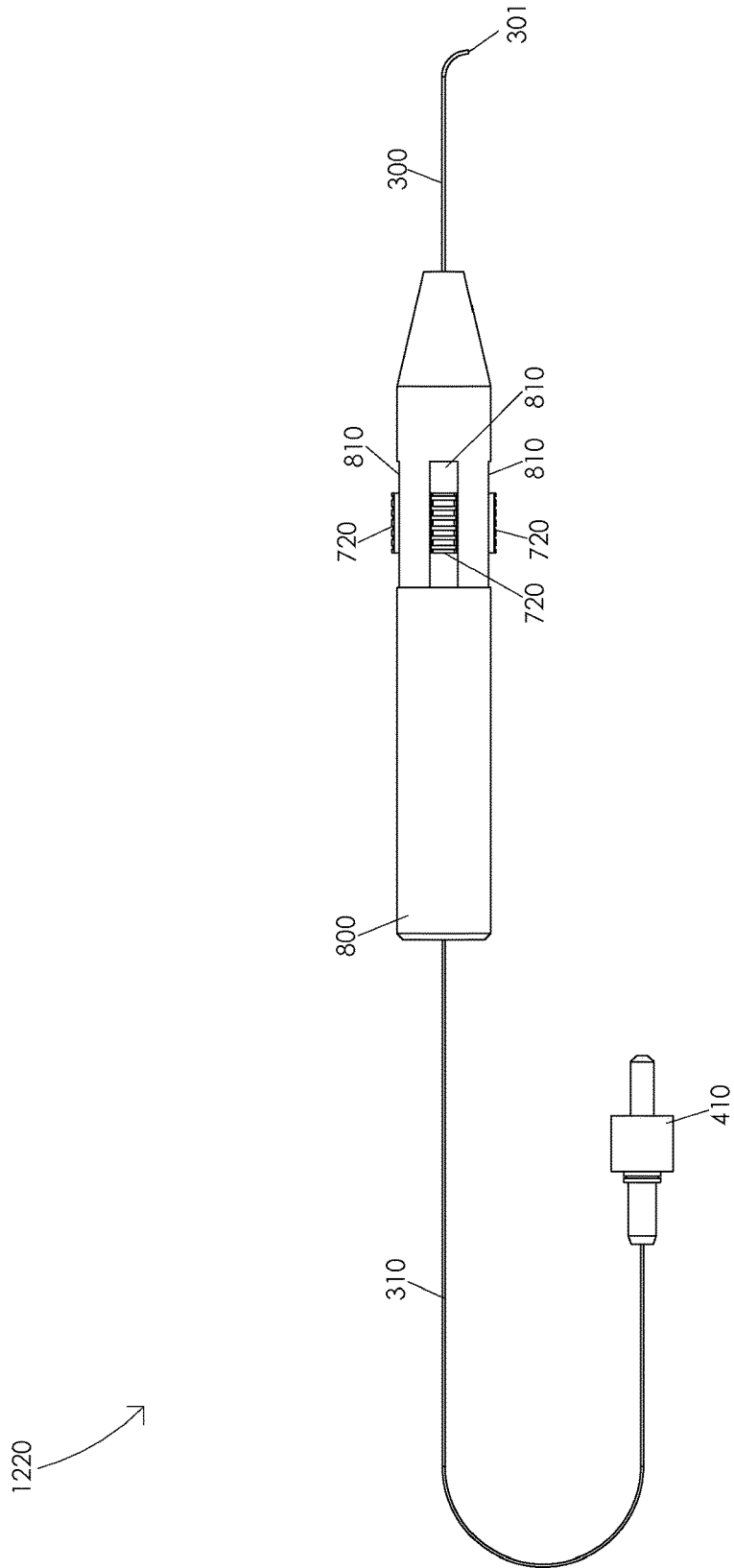

FIG. 12C illustrates an optic fiber in a second partially straightened position 1220. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a first partially straighten position 1210 to an optic fiber in a second partially straightened position 1220. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract flexible housing tube 300 relative to cable 910. Illustratively, a portion of cable 910, e.g., a portion of cable 910 fixed to a portion of flexible housing tube 300, may be configured to facilitate a retraction of flexible housing tube 300 relative to cable 910. In one or more embodiments, a retraction of flexible housing tube 300 relative to cable 910 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a first partially straightened position 1210 to an optic fiber in a second partially straightened position 1220. In one or more embodiments, a line tangent to optic fiber distal end 311 may intersect a line tangent to flexible housing tube proximal end 302 at a second partially straightened angle, e.g., when optic fiber 310 comprises an optic fiber in a second partially straightened position 1220. Illustratively, the second partially straightened angle may comprise any angle less than the first partially straightened angle. For example, the second partially straightened angle may comprise a 90 degree angle.

Figure 12D:
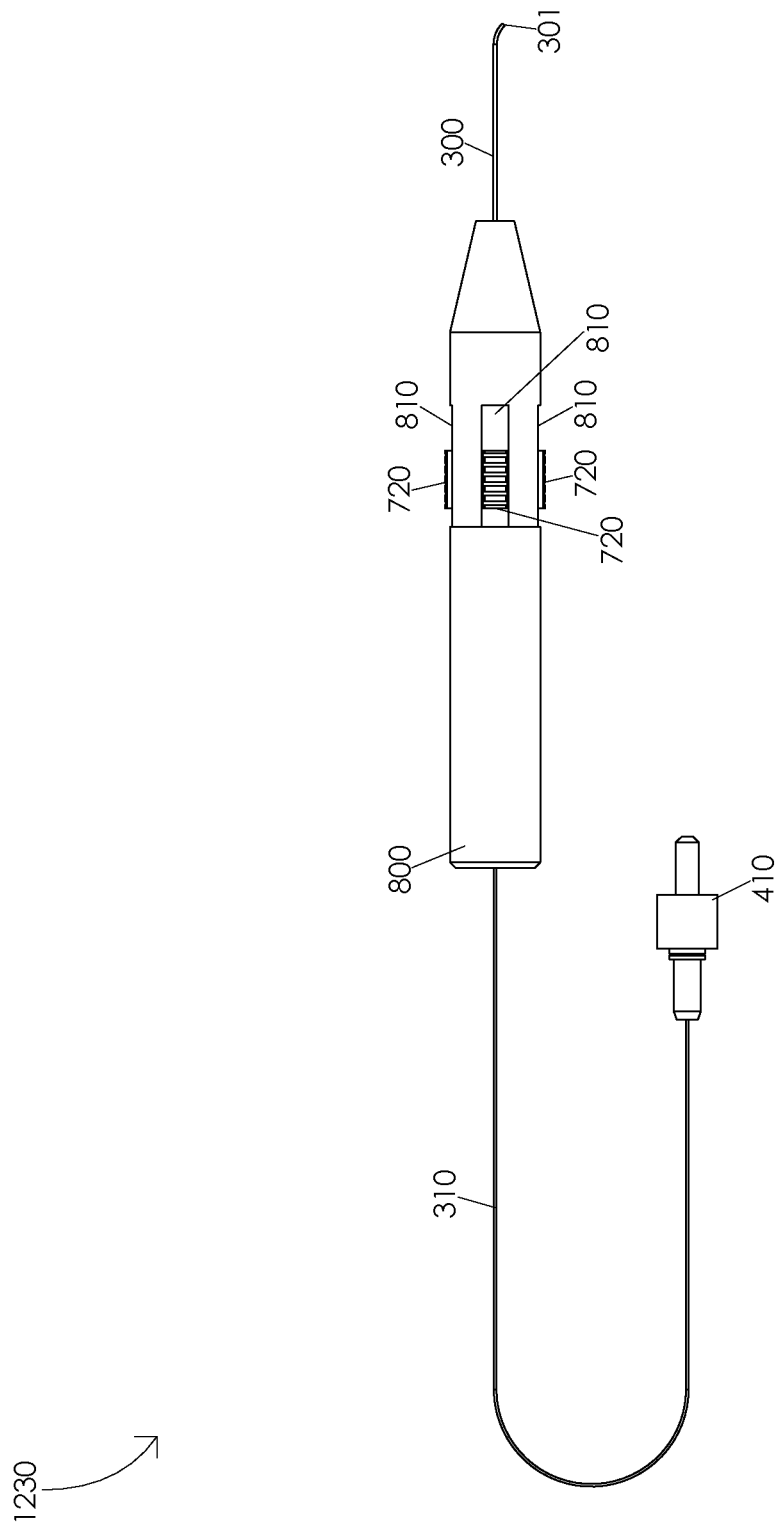

FIG. 12D illustrates an optic fiber in a third partially straightened position 1230. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a second partially straightened position 1220 to an optic fiber in a third partially straightened position 1230. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract flexible housing tube 300 relative to cable 910. Illustratively, a portion of cable 910, e.g., a portion of cable 910 fixed to a portion of flexible housing tube 300, may be configured to facilitate a retraction of flexible housing tube 300 relative to cable 910. In one or more embodiments, a retraction of flexible housing tube 300 relative to cable 910 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a second partially straightened position 1220 to an optic fiber in a third partially straightened position 1230. In one or more embodiments, a line tangent to optic fiber distal end 311 may intersect a line tangent to flexible housing tube proximal end 302 at a third partially straightened angle, e.g., when optic fiber 310 comprises an optic fiber in a third partially straightened position 1230. Illustratively, the third partially straightened angle may comprise any angle less than the second partially straightened angle. For example, the third partially straightened angle may comprise a 45 degree angle.

Figure 12E:
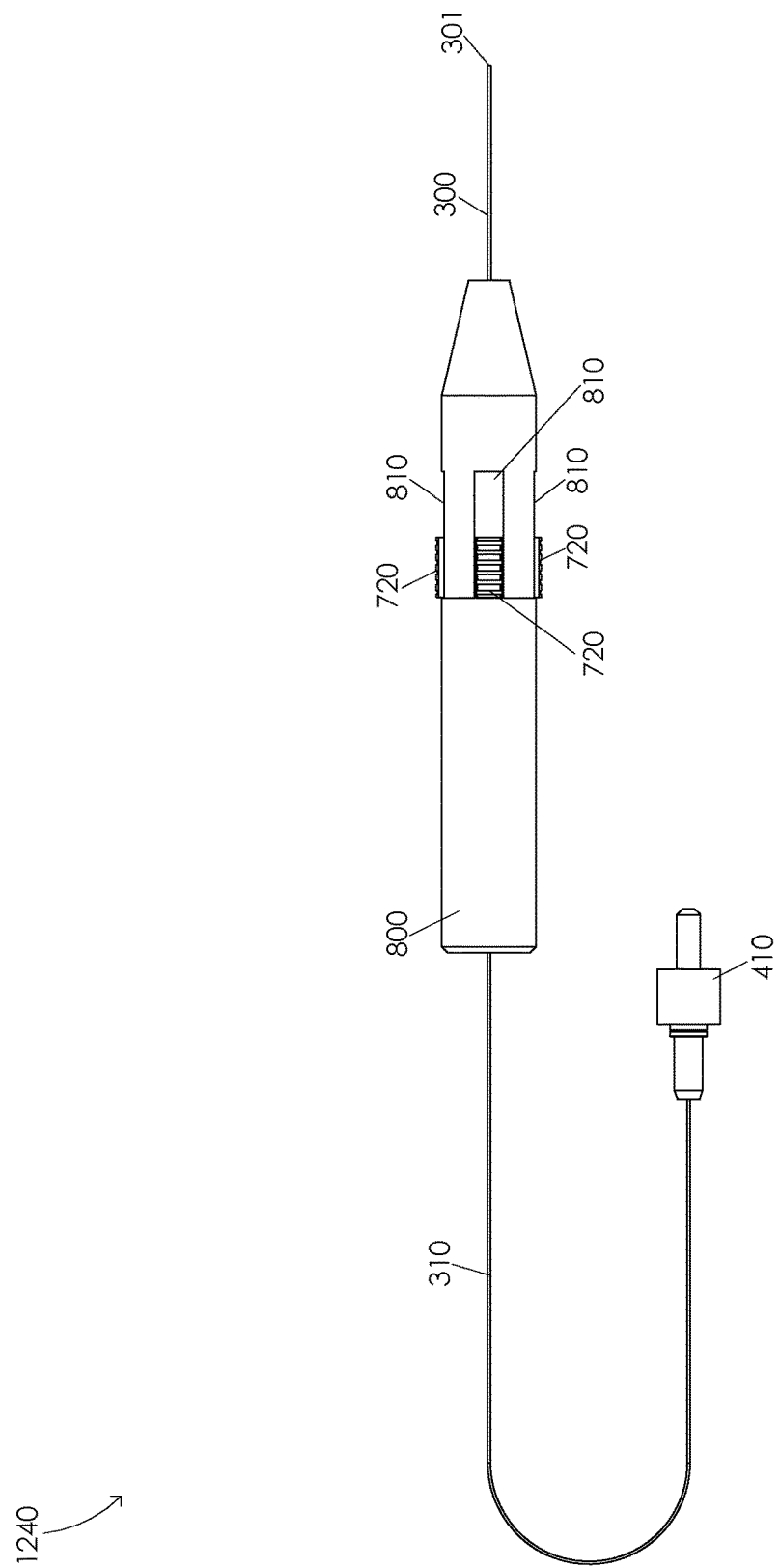

FIG. 12E illustrates an optic fiber in a fully straightened position 1240. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a third partially straightened position 1230 to an optic fiber in a fully straightened position 1240. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract flexible housing tube 300 relative to cable 910. Illustratively, a portion of cable 910, e.g., a portion of cable 910 fixed to a portion of flexible housing tube 300, may be configured to facilitate a retraction of flexible housing tube 300 relative to cable 910. In one or more embodiments, a retraction of flexible housing tube 300 relative to cable 910 may be configured to reduce a force applied to a portion of flexible housing tube 300. Illustratively, a reduction of a force applied to a portion of flexible housing tube 300 may be configured to cause flexible housing tube 300 to gradually straighten, e.g., by decompressing a portion of flexible housing tube 300. In one or more embodiments, a gradual straightening of flexible housing tube 300 may be configured to gradually straighten optic fiber 310, e.g., from an optic fiber in a third partially straightened position 1230 to an optic fiber in a fully straightened position 1240. In one or more embodiments, a line tangent to optic fiber distal end 311 may be parallel to a line tangent to flexible housing tube proximal end 302, e.g., when optic fiber 310 comprises an optic fiber in a fully straightened position 1240.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 800 to orient flexible housing tube 300 in an orientation configured to cause a curvature of flexible housing tube 300 within the particular transverse plane of the inner eye and varying an amount of actuation of an actuation control 720 of a plurality of actuation controls 720. Illustratively, a surgeon may aim optic fiber distal end 311 at any target within a particular sagittal plane of the inner eye by, e.g., rotating handle 800 to orient flexible housing tube 300 in an orientation configured to cause a curvature of flexible housing tube 300 within the particular sagittal plane of the inner eye and varying an amount of actuation of an actuation control 720 of a plurality of actuation controls 720. In one or more embodiments, a surgeon may aim optic fiber distal end 311 at any target within a particular frontal plane of the inner eye by, e.g., varying an amount of actuation of an actuation control 720 of a plurality of actuation controls 720 to orient a line tangent to optic fiber distal end 311 wherein the line tangent to optic fiber distal end 311 is within the particular frontal plane of the inner eye and rotating handle 800. Illustratively, a surgeon may aim optic fiber distal end 311 at any target located outside of the particular transverse plane, the particular sagittal plane, and the particular frontal plane of the inner eye, e.g., by varying a rotational orientation of handle 800 and varying an amount of actuation of an actuation control 720 of a plurality of actuation controls 720. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. A laser probe comprising:
   a handle having a handle distal end and a handle proximal end;
   an actuation mechanism guide of the handle;
   an actuation mechanism having an actuation mechanism distal end and an actuation mechanism proximal end wherein the actuation mechanism is disposed in the actuation mechanism guide and wherein the actuation mechanism is disposed between a handle end cap and a handle base;
   a proximal chamber of the handle;
   a flexible housing tube housing of the actuation mechanism;
   a plurality of actuation control guides of the handle wherein each actuation control guide of the plurality of actuation control guides has an actuation control guide distal end and an actuation control guide proximal end;
   a plurality of actuation controls wherein each actuation control of the plurality of actuation controls has an actuation control distal end and an actuation control proximal end and wherein each actuation control of the plurality of actuation controls is disposed in an actuation control guide of the plurality of actuation control guides and wherein an actuation of an actuation control of the plurality of actuation controls is configured to actuate each actuation control of the plurality of actuation controls;
   a single flexible housing tube having a flexible housing tube distal end and a flexible housing tube proximal end wherein the flexible housing tube proximal end is disposed in the flexible housing tube housing and wherein the flexible housing tube is fixed in the housing tube housing and wherein the flexible housing tube distal end extends from the handle distal end and wherein the flexible housing tube is manufactured from nitinol having an ultimate tensile strength in a range of 700 to 1000 MPa;
   a cable having a cable distal end and a cable proximal end wherein the cable is disposed in the handle and the flexible housing tube and wherein a portion of the cable is fixed in the flexible housing tube; and
   an optic fiber having an optic fiber distal end and an optic fiber proximal end wherein the optic fiber is disposed in the handle and the flexible housing tube and wherein an actuation of the actuation control of the plurality of actuation controls towards an actuation control guide distal end and away from an actuation control guide proximal end is configured to extend the flexible housing tube relative to the optic fiber proximal end and curve the optic fiber.

2. The laser probe of claim 1 wherein the actuation of the actuation control of the plurality of actuation controls towards the actuation control guide distal end and away from the actuation control guide proximal end is configured to curve the optic fiber less than 45 degrees.

3. The laser probe of claim 1 wherein the actuation of the actuation control of the plurality of actuation controls towards the actuation control guide distal end and away from the actuation control guide proximal end is configured to curve the optic fiber more than 45 degrees.

4. The laser probe of claim 1 wherein the actuation of the actuation control of the plurality of actuation controls towards the actuation control guide distal end and away from the actuation control guide proximal end is configured to curve the flexible housing tube.

5. The laser probe of claim 1 wherein the actuation of the actuation control of the plurality of actuation controls towards the actuation control guide distal end and away from the actuation control guide proximal end is configured to apply a force to a portion of the flexible housing tube.

6. The laser probe of claim 1 wherein the actuation of the actuation control of the plurality of actuation controls towards the actuation control guide distal end and away from the actuation control guide proximal end is configured to compress a portion of the flexible housing tube.

7. The laser probe of claim 1 wherein the actuation of the actuation control of the plurality of actuation controls towards the actuation control guide distal end and away from the actuation control guide proximal end is configured to actuate the actuation mechanism towards the handle distal end and away from the handle proximal end.

8. The laser probe of claim 1 wherein the actuation of the actuation control of the plurality of actuation controls towards the actuation control guide distal end and away from the actuation control guide proximal end is configured to extend the actuation mechanism relative to the optic fiber proximal end.

9. The laser probe of claim 1 wherein an actuation of the actuation control of the plurality of actuation controls towards the actuation control guide proximal end and away from the actuation control guide distal end is configured to straighten the optic fiber.

10. The laser probe of claim 1 wherein an actuation of the actuation control of the plurality of actuation controls towards the actuation control guide proximal end and away from the actuation control guide distal end is configured to straighten the optic fiber less than 45 degrees.

11. The laser probe of claim 1 wherein an actuation of the actuation control of the plurality of actuation controls towards the actuation control guide proximal end and away from the actuation control guide distal end is configured to straighten the optic fiber more than 45 degrees.

12. The laser probe of claim 1 wherein an actuation of the actuation control of the plurality of actuation controls towards the actuation control guide proximal end and away from the actuation control guide distal end is configured to straighten the flexible housing tube.

13. The laser probe of claim 1 wherein an actuation of the actuation control of the plurality of actuation controls towards the actuation control guide proximal end and away from the actuation control guide distal end is configured to retract the flexible housing tube relative to the optic fiber proximal end.

14. The laser probe of claim 1 wherein an actuation of the actuation control of the plurality of actuation controls towards the actuation control guide proximal end and away from the actuation control guide distal end is configured to reduce a force applied to a portion of the flexible housing tube.

15. The laser probe of claim 1 wherein an actuation of the actuation control of the plurality of actuation controls towards the actuation control guide proximal end and away from the actuation control guide distal end is configured to decompress a portion of the flexible housing tube.

16. The laser probe of claim 1 wherein an actuation of the actuation control of the plurality of actuation controls towards the actuation control guide proximal end and away from the actuation control guide distal end is configured to actuate the actuation mechanism towards the handle proximal end and away from the handle distal end.

17. The laser probe of claim 1 wherein an actuation of the actuation control of the plurality of actuation controls towards the actuation control guide proximal end and away from the actuation control guide distal end is configured to retract the actuation mechanism relative to the optic fiber proximal end.

18. The laser probe of claim 1 further comprising:
   a light source interface configured to interface with the optic fiber proximal end.

19. The laser probe of claim 18 where in the light source interface is an SMA connector.

20. The laser probe of claim 1 further comprising:
   a polyimide buffer of the optic fiber.

* * * * *